(12) United States Patent
Ilan

(10) Patent No.: US 7,897,580 B2
(45) Date of Patent: Mar. 1, 2011

(54) β GLYCOLIPIDS AS IMMUNO-MODULATORS

(76) Inventor: Yaron Ilan, Jerusalem (IL)

( * ) Notice: Subject to any disclaimer, the term of this patent is extended or adjusted under 35 U.S.C. 154(b) by 1315 days.

(21) Appl. No.: 11/287,502

(22) Filed: Nov. 25, 2005

(65) Prior Publication Data

US 2007/0117778 A1 May 24, 2007

(30) Foreign Application Priority Data

Nov. 24, 2005 (IL) .................................... 172175

(51) Int. Cl.
*A61K 31/70* (2006.01)
*A61K 31/13* (2006.01)
*C07H 5/04* (2006.01)
*C09F 7/00* (2006.01)

(52) U.S. Cl. ................. 514/25; 514/613; 536/18.7; 554/35

(58) Field of Classification Search ................. None
See application file for complete search history.

(56) References Cited

U.S. PATENT DOCUMENTS

| 5,686,426 | A | 11/1997 | Martel et al. |
| 7,488,491 | B2 * | 2/2009 | Tsuji et al. ............ 424/278.1 |

FOREIGN PATENT DOCUMENTS

| EP | 0 718 787 A1 * | 7/1996 |
| EP | 1452181 | 9/2004 |
| WO | WO 00/24406 | 5/2000 |
| WO | WO 02/051986 A2 * | 7/2002 |
| WO | WO 2005/014008 | 2/2005 |
| WO | WO 2005/032462 A2 | 4/2005 |

OTHER PUBLICATIONS

Sigma Biochemicals and Reagents for Life Science Research Catalog, St. Louis, MO, 2000-2001, only pp. 226-227 supplied.*
Nelson & Cox, "Lehninger—Principles of Biochemistry, 4th Edition," W. H. Freeman and Co., New York, NY, 2005, only pp. 352-353 supplied.*
Lehninger, A. L., "Biochemistry—The Molecular Basis of Cell Structure and Function, 2nd Edition," Worth Publishers, Inc., New York, NY, Jul. 1978, only pp. 676-677 supplied.*
Hara et al., "Occurrence of Sulfatide as a Major Glycosphingolipid in WHHL Rabbit Serum Lipoproteins," The Journal of Biochemistry (Japan), 102(1), 83-92 (Jul. 1987).*
International Search Report for PCT/IL2006/001217 (claiming priority to same Israeli case), Mar. 21, 2007.
International Preliminary Report on Patentability for PCT/IL2006/001217, Mar. 21, 2007.
Adorini, L. et al. Immunol. Today, Pathogenesis and Immunotherapy of autoimmune diseases, vol. 18:209-211 (1997).
Angulo, P. N. Eng. J. Med., Nonalcoholic Fatty Liver, vol. 346, No. 16:1221-1231 (2002).
Bleicher, P.A. et al., Science, Expression of Murine CD1 on Gastrointestinal Epithelium, vol. 250:679-682 (1990).
Caldwell, S.H. et al., Hepatology, Cryptogenic Cirrhosis: Clinical Characterization and Risk Factors for Underlying Disease, vol. 29:664-669 (1999).
Chandra, R.K. et al., Acta. Paediatr. Scand, Immunocompetence in Obesity, vol. 69:25-30 (1980).
Chiba, M. et al. Gut, Human colonic intraepithelial and lamina proprial lymphocytes:cytotoxicity in vitro and the potential effects . . . vol. 22:177-186 (1981).
Cohen, B. et al., Science, Modulation of Insulin Activities by Leptin, vol. 274:1185-1188 (1996).
Collins, C. et al., Eur. J. Immunol., RAG1, RAG2 and pre-T cell receptor α chain expression by adult human hepatic T cells: evidence for extrathymic T cell maturation, vol. 26:3114-3118 (1996).
Cortez-Pinto, H. et al., JAMA, Alterations in Liver ATP Homeostasis in Human Nonalcoholic Steatohepatitis, vol. 282, No. 17:1659-1664 (1999).
Das, K.M., et al. Gastroenterology, A Shared and Unique Epitope(s) on Human Colon, Skin, and Biliary Epithelium Detected by a Monoclonal Antibody, vol. 98:464-469 (1990).
Dasgupta, A. et al. Gut, Circulating immunoglobulin G1 antibody in patients with ulcerative colitis against the colonic epithelial protein detected by a novel monoclonal antibody, vol. 35:1712-1717 (1994).
Diehl, A.M. Am. J. Physiol. Gastrointest. liver Physiol.,Nonalcoholic Steatosis and Steatohepatitis: IV. Nonalcoholic fatty liver disease abnormalities . . . vol. 282:G1-G5 (2002).
Faggioni, R. et al., Proc. Natl. Acad. Sci. USA, Leptin-deficient (ob/ob) mice are protected from T cell-mediated hepatotoxicity . . . vol. 97:2367-2372 (2000).
Feingold, K.R. et al., Diabetes, Role of Cytokines in Inducing Hyperlipidemia, vol. 41:97-101 (1992).
Field, C.J. et al., Am. J. Clin. Nutr., Changes in circulating leukocytes adn mitogen responses during very-low-energy all-protein reducing diets, vol. 54:123-129 (1991).
George, D.K. et al., Gastroenterology, Increased Hepatic Iron Concentration in Nonalcoholic Steatohepatitis . . . vol. 114:311-318 (1998).
Hibi, T. et al., Clin. Exp. Immunol.,Circulating antibodies to the surface antigens on colon epithelial cells in ulcerative colitis, vol. 54:163-168 (1983).

(Continued)

*Primary Examiner* — Lawrence E Crane
(74) *Attorney, Agent, or Firm* — Natalie Bogdanos

(57) ABSTRACT

The invention relates to the use of β-glycolipids as immunomodulators. More particularly, the invention relates to the use of β-glycolipids, preferably, β-lactosyl-ceramide, β-glucosylceramide, β-galactosyl-ceramide, ceramid and β-lactosyl-ceramide, as well as any mixture or combination thereof for the treatment of immune related disorders. The present invention further relates to a process for the modulation of the Th1/Th2 cell balance toward anti-inflammatory cytokine producing cells, in a subject suffering from an immune related disorder. Therapeutic compositions and method for the preparation of these compositions are also provided.

16 Claims, 6 Drawing Sheets

OTHER PUBLICATIONS

Hotamisligil, G.S. et al., Journal of Internal Medicine, The role of TNF α and TNF receptors in obesity and insulin resistance, vol. 245:621-625 (1999).

Hotamisligil, G.S. et al., Science, Adipose Expression of Tumor Necrosis Factor- α : Direct Role in Obsesity-Linked Insulin Resistance, vol. 259:87-91 (1993).

Howard, J.K. et al, J. Clin. Invest., Leptin protects mice from starvation-induced lymphoid atrophy and increases thymic cellularity in ob/ob mice, vol. 104:1051-1059 (1999).

Hruszkewycz, A.M. Biochem. Biophys. Res. Commun., Evidence for Mitochondrial DNA Damage by Lipids Peroxidation, vol. 153:191-197(1988).

Koffler, M. et al., Diabetes, Immunobiological Consequence of Regulation of Insulin Receptor on Alloactivated Lymphocytes in Normal and Obese Subjects, vol. 40:364-370 (1991).

Krishnan, E.C. et al., J. Surg. Res., Study of Function and Maturation of Monocytes in Morbidly Obese Individuals vol. 33:89-97 (1982).

Loffreda, S. et al., FASEB J.,, Leptin regulates prooinflammatory immune responses, vol. 12:57-65 (1998).

Lord, G.M. et al., Nature, Leptin modulates the T-cell immune response and reverses starvation-induced immunosupression, vol. 394:897-901 (1998).

Mabuchi, A. et al., J. Leukocyte Biology, Role of the liver in T cell differentiation—generation of CD3-CD4+/CD8+TCR β -cells and CD3-4-8-TCRβ +cells from CD4-8-TCRB -athymic nude bone marrow cells by culture with parenchymal liver cells vol. 63:575-583 (1998).

Madsen, K.L. et al., Gastroenterology, Interleukin 10 Prevents Cytokine-Induced Disruption of T84 Monolayer Barrier Integrity and Limits Chloride Secretion, vol. 113:151-159 (1997).

Mattacks, C.A. et al., Cytokine, Interactions of Noradrenalin and Tumour Necrosis Factor α, Interleukin 4 and Interleukin 6 in the Control of Lipolysis from adipocytes around lymph nodes, vol. 11, No. 5:334-346 (1999).

Matteoni, C.A. et al., Gastroenterology, Nonalcoholic Fatty Liver Disease: A Spectrum of Clinical and Pathological Severity, vol. 116:1413-1419 (1999).

Mitchell, D.G. et al., Invest. Radiol., Chemical Shift Phase-Difference and Suppression Magnetic Resonance Imaging Techniques in Animals, Phantoms, and Humans, vol. 26:1041-1052 (1991).

Mizoguchi, A., et al., J. Exp. Med., Cytokine Imbalance and Autoantibody Production in T Cell Receptor- α Mutant Mice with Inflammatory Bowel Disease vol. 183:847-856, (1996).

Montague, C.T. et al., Diabetes, Depot-Related Gene Expression in Human Subcutaneous and Omental Adipocytes, vol. 47:1384-1391 (1998).

Neurath, M. et al., J. Exp. Med., Experimental Granulomatous Colitis in Mice Is Abrogated by Induction of TGF- α -mediated Oral Tolerance, vol. 183:2605-2616 (1996).

Hiroko Ogawa et al, Biochimica et Biophysica Acta, Cachectin/tumor necrosis factor and interleukin-1 show different . . . , vol. 1003 (1989) 131-135.

Pelleymounter, M.A. et al., Science, Effects of the obese Gene Product on Body Weight Regulation in ob/ob Mice, vol. 269:540-543 (1995).

Podolsky, D.K. et al., New Engl. J. Med., Inflammatory Bowel Disease, vol. 325:928-937(1991).

Pond, C.M. et al., Proceedings of the nutrition society, Long-term changes in adipose tissue in human disease, vol. 60:365-374 (2001).

Powrie, F. et al., Immunity, Inhibition of Th1 Responses Prevents Inflammatory Bowels Disease in scid Mice Reconstituted with CD45RBhi CD4+ T Cells vol. 1:553-562 (1994).

Purohit, A. et al., Journal of Clinical Endocrinology and Metabolism, Aromatase Activity and Interleukin-6 Production by Normal and Malignant Breast Tissues, vol. 80:3052-58 (1995).

Raedler, A. et al., Clin. Exp. Immunol., Elevated numbers of peripheral T cells in inflammatory bowel diseases displaying T9 antigen and Fc α receptors, vol. 60:518-524 (1985).

Rosen, B.S. et al., Science, Adipsin and complement factor D activity: an immune-related defect in obsity vol. 244:1483-7 (1989).

Sadlack, B. et al.,Cell, Ulcerative Colitis-like Disease in Mice with a Disrupted Interleukin-2 Gene vol. 75:253-261 (1993).

Sanyal, A.J. et al., Gastroenterology, Nonalcoholic Steatohepatitis: Association of Insulin Resistance and Mitochondrial Abnormalities, vol. 120:1183-1192 (2001).

Sarraf, P. et al., Journal of experimental medicine, Multiple Cytokines and Acute Inflammation Raise Mouse Leptin Levels: Potential Role in Inflammatory Anorexia, vol. 185:171-175 (1997).

Strober, W. et al., Immunol. Today, Reciprocal IFN- γ and TGF- β responses regulate the occurrence of mucosal inflammation, vol. 18:61-64 (1997).

Takahashi, F. et al., J. Clin. Invest., Isolation and Characterization of a Colonic Autoantigen Specifically Recognized by Colon Tissue-bound Immunoglobulin G from Idiopathic Ulcerative Colitis, vol. 76:311-318 (1985).

Namimoto, T. et al., Radiology, Adrenal Masses: Quantification of Fat Content with Double-Echo Chemical Shift In-Phase and Opposed-Phase FLASH MR Images for . . . , vol. 218:642-646 (2001).

Trop, S. et al., Hepatology, Liver-Associated Lymphocytes Expressing NK1.1 Are Essential for Oral Immune Tolerance Induction in a Murine Model, vol. 29:746-755 (1999).

Uysal, et al. Nature, Protection from obesity-induced insulin resistance in mice lacking TNF- α function, vol. 389:610-614 (1997).

Van Deventer S. J. et al., Gastroenterology, Multiple Doses of Intravenous Interleukin 10 in Steroid-Refractory Crohn's Disease, vol. 113:383-389 (1997).

Vicari, A.P. et al., Immunology Today, Mouse NK1.1 +T cells: a new family of T cells, vol. 17(2):71-76 (1996).

Weiner, H.L. et al., Immunol. Today, Oral Tolerance: immune mechanisms and treatment of autoimmune diseases, vol. 18: 335-343 (1997).

Yang, S. Q. et al., Proc Natl Acad Sci USA, Obesity increases sensitivity to endotoxin liver injury: Implications for the pathogenesis of steatohepatitis, vol. 94:2557-2562 (1997).

Zhang, Y. et al., Nature, Positional cloning of the mouse obese gene and its human homologue, 372:425-432 (1994).

Zhiping, L.I. et al., Gastroenterology, Murine Leptin Deficiency Alters Kupffer Cell Production of Cytokines That Regulate the Innate Immune Syste, vol. 123:1304-1310 (2002).

Ogawa, H. et al., Biochimica et biophysica acta, Cachectin/tumor necrosis factor and interleukin-1 show different modes of combined effects on lipoprotein lipase activity and intracellular lipolysis in 3T3-L1 cells, vol. 1003: 131-135 (1989).

* cited by examiner

β GLYCOLIPIDS AS IMMUNO-MODULATORS

CROSS-REFERENCE TO RELATED U.S. APPLICATIONS

This application claims priority to Israeli Application No. 1,721,17, filed Nov. 24, 2005, which is incorporated by reference in its entirety herein.

FIELD OF THE INVENTION

The invention relates to the use of β-glycolipids as immunomodulators. More particularly, the invention relates to the use of β-glycolipids, preferably, β-lactosyl-ceramide, β-glucosylceramide, β-galactosyl-ceramide, ceramid, and most preferably, β-lactosyl-ceramide, as well as any mixture or combination thereof for the treatment of immune related disorders.

BACKGROUND OF THE INVENTION

Immune therapy involves the exposure of components of the immune system to various elements (cytokines, disease associated antigens and natural metabolites) to combat disease processes in which a dysregulated immune response is thought to play a role. Immune dysregulation is thought to play a major part in the pathogenesis or disease course of a great number of disease processes, including various neoplastic, inflammatory, infectious and genetic entities.

These disorders can be perceived as a dysbalance between pro-inflammatory (Th1) and anti-inflammatory (Th2) cytokines, and few of them are described herein below.

The role of the Immune System in the Pathogenesis of Inflammatory Bowel Disease

Inflammatory bowel diseases (IBD) are common gastrointestinal disorders, that can be perceived as being the result of a dysbalance between Th1-pro-inflammatory, and Th2-anti-inflammatory subtypes of immune responses [Strober, W., et al., Immunol Today 18:61-64 (1997); Neurath, M., et al., J. Exp. Med. 183:2605-2616 (1996)].

There are several extra-intestinal manifestations that accompany IBD, for example: autoimmune phenomena; immune complexes have a role in target organ damage; and, immunosuppressive agents such as glucocorticoids, azathioprine, methotrexate and cyclosporin are used to alleviate the disease [Podolsky, D. K., et al., New Engl. J. Med., 325:928-935(1991); Strober, W., et al., In Clinical Immunology, Mosby, St. Louis. R. R. Rich, Editor, 1401-14281-2 (1995)]. Patients with IBD have antibodies against components of colon cells and several different bacterial antigens. These antigens gain access to the immune system as a consequence of epithelial damage [Hibi, S., et al., Clin. Exp. Immunol. 54:163-168 (1983); Das, K. M., et al., Gastroenterology 98:464-69 (1990)]. Abnormalities of T cell-mediated immunity, including coetaneous anergy and diminished responsiveness to T cell stimuli, have also been described in these patients [Chiba, M., et al. Gut, 22:177-182 (1981); Raedler, A., et al., Clin. Exp. Immunol. 60:518-526 (1985)]. In addition, changes in mucosal cell mediated immunity were identified, including increased concentrations of mucosal IgG cells and changes in T cells subsets, suggesting antigen stimulation [Dasgupta, A., et al., Gut 35:1712-17 (1994); Takahashi, F., et al., J. Clin. Invest. 76:311-318 (1985)]. Exposure of target antigens after infectious, immune, or toxic damage, leads to activation of mucosal immune cells resulting in cytokines that lead to mucosal inflammatory response [Neurath, M., et al., J. Exp. Med., 183:2605-2616 (1996)]. Secretion of pro-inflammatory cytokines such as IFNγ, contributes to an increase in mucosal permeability, and has been described in animal models of IBD [Strober, W., et al., Immunol. Today 18:61-64. (1997)]. Similarly, an increase in collagen synthesis mediated by IL1 and IL6 can be detected in these animals [Strober, W., et al., ibid.]. A Th1-mediated granulomatous colitis model has been established by the adoptive transfer of normal CD45RB T cells from Balb/C mice into CB-17 scid mice. CD4 cells from CD45RB were shown to prevent the disease when injected together with the CD45RB population. This prevention could be reversed by adding antibodies to TGFβ1 [Sadlack, B., et al., Cell 75:253-261 (1993); Powrie, F., et al., Immunity 1:553-562 (1994)].

The Th1/Th2 Dysbalance in Inflammatory Bowel Disease

Both CD4 and CD8 lymphocytes can be typed as either Th1 cells that produce IL-2 and IFNγ, or Th2 cells that produce IL-4, and IL-10. The way the immune system responds to foreign and self antigens, is the result of a balance between the two subtypes of responses [Weiner, H. L., et al., Immunol. Today 18: 335-343 (1997); Adorini, L., et al., Immunol. Today 18:209-211 (1997)]. A Th1 type response is involved in the pathogenesis of several autoimmune and chronic inflammatory disorders such as IBD [Adorini, L., et al., (1997) ibid.; Mizoguchi, A., et al., J. Exp. Med. 183:847-856, (1996)]. Thus experimental colitis and IBD in humans can be perceived as a dysbalance between pro-inflammatory Th1-type and anti-inflammatory Th2-type cytokines. It has been recently shown, in both animals and humans, that anti-inflammatory cytokines such as IL10 can downregulate the pro-inflammatory effects of Th1-mediated cytokines, thereby alleviating immune-mediated disorders [Mizoguchi, A., et al., (1996) ibid.; Madsen, K. L., et al., Gastroenterology 113: 151-159 (1997); Van Deventer Sander, J., et al., Gastroenterology 113:383-389 (1997)].

The Role of the Immune System in the Pathogenesis of Non-Alcoholic Steatohepatitis Non-alcoholic steatohepatitis (NASH) is a clinico-pathological entity consisting of hepatic fat accumulation, inflammation and fibrosis in patients who have no history of alcohol consumption. It may progress to cirrhosis in 20% of cases and is considered the most common cause of cryptogenic cirrhosis in the Western world [Caldwell, S. H. et al., Hepatology 29:664 (1999); Matteoni, C. A. et al., Gastroenterology 116: 1413 (1999)]. NASH is common in patients who suffer of other metabolic disturbances, which are suggested to play a contributing role in the pathogenesis of the disorder. These include insulin resistance [Sanyal, A. J. et al., Gastroenterology 120:1183 (2001)], obesity-related ATP depletion [Cortez-Pinto, H. et al., Jama 282:1659 (1999)], increased free-fatty-acid beta peroxidation [Hruszkewycz, A. M. Biochem. Biophys. Res. Commun. 153:191 (1988)], iron accumulation [George, D. K. et al., gastroenterology 114:311 (1998)], antioxidant depletion [Harrison, S. A. et al., gastroenterology 123:M1332 (2002)], and leptin deficiency [Cohen, B. et al., Science 274:1185 (1996)]. Yet no therapeutic intervention, including weight loss, tight diabetic control, normalization of lipid levels and antioxidant treatment have consistently shown an alteration in the natural progression of the disorder [Angulo, P. New England Journal of Medicine 346:1221-1231 (2002)].

Most information about NASH has been derived from two mammalian models: leptin-deficient ob/ob mice and leptin-receptor deficient fa/fa Zucker rats. Leptin is a protein that is involved with the regulation of body weight [Zhang, Y. et al., Nature 372:425-432 (1994)]. Its deficiency in rodents and humans results in a severe form of 'metabolic syndrome' (formerly termed syndrome X) consisting of morbid obesity, glucose intolerance, hyperlipidemia, and severe hepatic steatosis [Pelleymounter, M. A. et al., Science 269:540-543 (1995)]. Yet, as mentioned above, no intervention aimed at correcting some of these metabolic disturbances have resulted in an amelioration of the hepatic steatosis, fibrosis, and inflammation.

Recent evidence suggests that the immune system may play a pivotal role in the pathogenesis of NASH in the leptin deficient models. In leptin deficient mice, defective hepatic macrophage (Kupffer cell) response has been observed after liver injury induction by lipopolysaccharide [Diehl, A. M. J. Physiol. Gastrointest. liver Physiol. 282:G1-G5 (2002)]. In similar models, LPS induction of IL6 was greatly enhanced, while that of IL10 was inhibited [Loffreda, S, et al., FASEB J. 12:57-65 (1998)]. Ob/ob mice hepatic macrophages were observed to produce more IL12 and less IL15 than control mice in response to LPS challenge, which may explain the significant reduction in the number and function of NKT lymphocytes observed in these mice [Yang et al., Proc Natl Acad Sci USA 94:2557-2562 (1997)]. Other observations have shown a reduction in the number of CD4 T lymphocytes in the blood and liver of leptin-deficient ob/ob mice [Howard, J. K. et al, J. Clin. Invest. 104:1051-1059 (1999) and Lord, et al., Nature 394:897-901 (1998)]. This may explain the relative resistance of leptin-deficient mice to Concanavalin A hepatitis, which is mediated by CD4 T lymphocytes [Faggioni, R. et al., Proc. Natl. Acad. Sci. USA 97:2367-2372 (2000)].

The Th1/Th2 Dysbalance in Non-Alcoholic Steatohepatitis

CD4 and CD8 lymphocytes are classified as either Th1 cells that produce IL-2 and IFNγ, or Th2 cells that produce IL-4 and IL-10. The immune system responds to foreign and self-antigens by a shift in balance between the two subtypes of responses [Weiner, H. L. et al., Immunol. Today 18: 335-343 (1997); Adorini, L. et al., Immunol. Today 18:209-211 (1997)]. Usually the Th1 type response causes a pro-inflammatory reaction [Adorini, L. et al., (1997) ibid.; Mizoguchi, A., et al., J. Exp. Med. 183:847-856, (1996)], while anti-inflammatory cytokines such as IL10 shift the balance towards an anti-inflammatory Th2 reaction, thereby alleviating immune-mediated disorders [Mizoguchi, A. et al., (1996) ibid.; Madsen, K. L. et al., Gastroenterology 113:151-159 (1997); Van Deventer Sander, J. et al., Gastroenterology 113: 383-389 (1997)]. NKT cells, in response to different endogenous and exogenous stimuli, are believed to play a major role in the direction of the immune system towards either the Th1 or Th2 pathways.

Leptin has been shown to play a major role in the immune regulation of the balance between Th1 & Th2 response (Lord, G. M. et al., Nature 394:897-901 (1998)]. In the leptin-deficient ob/ob mice NASH model an alteration of the number and function of NKT cells has been suggested to tilt the immune system towards the Th1 response. This is suggested to result in an increased sensitivity to LPS induced hepatotoxicity and a unique resistance to the hepatotoxic effects of Concanavalin A. The difference may be in their different pathogenic mechanisms. The former depends upon the action of the innate hepatic immune system, which is hyperactive in the leptin-deficient mice, while the latter is dependent upon the activation of NKT-lymphocytes, which are suppressed and defective in the leptin deficient mice [Faggioni, R. et al., PNAS 97:2367-2372 (2000), Zhiping, L. I. et al., Gastroenterology 123:1304-1310 (2002)].

The Immune System and Obesity

The immune system and the regulation of adipose tissue metabolism appear to be closely interlinked. Up to fifty percent of cells within adipose tissues are composed of non-adipose cells, including many immunocytes [Montague, C. T. et al., Diabetes 47:1384-91 (1998)]. Most research has been focused on the immunological consequences of morbid obesity. Immunological alterations which are known to exist in obese animals and humans include reduced DTH and mitogen-stimulated lymphocyte proliferation responses [Chandra, R. K. et al., Acta. Paediatr. Scand 69:25-30 (1980)], impaired phagocyte number and function [Krishnan, E. C. et al., J. Surg. Res. 33:89-97 (1982)], attenuation of insulin induced lymphocyte cytotoxicity [Koffler, M. et al., Diabetes 40:364-360 (1991)], and changes in the CD4/CD8 ratio, especially during weight loss attempts [Field, C. J. et al., Am. J. Clin. Nutr. 54:123-129 (1991)].

Adipose cells are known to secrete pro-inflammatory cytokines including TNF-β [Hotamisligil, G. S. et al., Science 259:87-91 (1993)] and IL6 [Purohit, A. et al., Journal of Clinical Endocrinology and Metabolism 80:3052-58 (1995)], which are both related to the level of adiposity [Hotamisligil, G. S. et al., Journal of Internal Medicine 245:621-625 (1999)]. Some of these cytokines are considered to have metabolic effects such as insulin resistance mediated by TNF-β [Ogawa, H. et al., Biochimica et biophysica acta 1003: 131-135 (1989)] and lipoprotein lipase inhibition mediated by IL6 [Feingold, et al., Diabetes 41:97s-101s (1992)]. TNF-β knockout mice have higher insulin sensitivity and improved lipid profile than their normal littermates [Uysal, et al., Nature 389:610-614 (1997)]. Other components of the immune system, which are produced by adipose cells, include the protein adipsin, which is an integral part of the alternative complement system, and functions identically to human complement factor D [Rosen, B. S. et al., Science 244:1483-7 (1989)].

Little information is known about the role of the immune system as a mediator of obesity, but several recent studies suggest that the immune system may have an important contributory role in the development of obesity. Several cytokines are known to act as adipose tissue regulators. TNF-β suppresses the expression of $\beta_3$ adreno-receptors on adipose cells, which are involved in sympathetically mediated lipolysis, while IL1 stimulates adipose leptin secretion [Sarraf, et al., Journal of experimental medicine 185:171-175 (1997)]. The metabolic activity rate of adipose cells has been observed to be closely correlated to their distance from the closest lymph node [Pond, C. M. et al., Proceedings of the nutrition society 60:365-374 (2001)], through a mechanism which is partly mediated by IL4, IL6 and TNF-β [Mattacks, C. A. et al., Cytokine 11:334-346 (1999)].

These observations, which point to the fact that obese animals and humans may also be suffering of various alterations in the different arms of the immune system, suggest that modulation of the immune system may change some of the pathogenic mechanisms responsible for the development of morbid obesity.

To the best of the inventor's knowledge, previously employed methods of immune modulation have not involved exposure of components of the immune system to mammalian naturally occurring β-glycolipids and specifically to a mixture of β-glycolipids.

WO 2005/032462, which is a previous publication by the present inventors, discloses the general use of intermediary metabolites and preferably, glucocerebrosides, in the treatment of immune-related disorders. The present invention now clearly shows that certain intermediary metabolites, the β-glycolipids and not the α-glycolipids are particularly effective, and specifically, β-lactosyl-ceramide (LacC), β-glucosylceramide (GluC), and β-galactosyl-ceramide (GalC)] and ceramide. Surprisingly, the inventors have now showed for the first time that β-lactosyl-ceramide may be used as a preferred β-glycolipid for immune-modulation.

Moreover, the inventors show a clear synergistic effect of a particular combination of two β-glycolipids, preferably a mixture of β-lactosyl-ceramide with β-glucosylceramide, which may be used as a powerful medicament for the treatment of immune-related disorders.

These and other objects of the invention will become clearer as the description proceeds

SUMMARY OF THE INVENTION

As a first aspect, the present invention relates to a process for the modulation of the Th1/Th2 cell balance toward anti-inflammatory cytokine producing cells, in a subject suffering from an immune related disorder. This process comprises the step of increasing the intracellular, extra-cellular or serum level of a naturally occurring β-glycolipid in a subject in need thereof. The modulation of the Th1/Th2 cell balance may be mediated by at least one component of said subject immune system. According to this embodiment, increasing the intracellular, extra-cellular or serum level of a naturally occurring β-glycolipid in said subject may be performed by:

(I) administering an effective amount of any one of: a β-glycolipid, a mixture of at least two β-glycolipids, a substance which increases the intracellular, extracellular or serum level of a naturally occurring β-glycolipid, and any combination of the above; or (II) exposing at least one component of said subject immune system to an effective amount of any one of: a β-glycolipid; a mixture of at least two β-glycolipids; a substance which increases the intracellular, extracellular or serum level of a naturally occurring β-glycolipid, and any combination of the above; or (III) any combination of the above.

In a second aspect, the invention relates to a method for the treatment of immune-related disorder in a mammalian subject in need thereof. According to one embodiment, the method of treatment comprises the step of administering to said subject an effective amount of any one of β-glycolipids, a mixture of at least two naturally occurring β-glycolipids and a substance which increases the intracellular, extracellular or serum level of a naturally occurring β-glycolipid, and of a composition comprising the same.

The invention further provides a method for the treatment of immune-related disorder in a mammalian subject in need thereof. According to this preferred embodiment, the method of the invention comprises the step of increasing the intracellular, extra-cellular or serum level of a naturally occurring β-glycolipid in said subject, by exposing at least one component of said subject immune-system to an effective amount of any one of: (a) a β-glycolipid (b) a mixture of at least two β-glycolipids (c) a substance which increases the intracellular, extracellular or serum level of a naturally occurring β-glycolipid; and (d) any combination of the above.

In a third aspect, the invention relates to a therapeutic composition for the treatment of an immune-related disorder in a mammalian subject. According to one embodiment, the composition of the invention may comprise as an active ingredient: (a) β-glycolipid, a mixture of at least two β-glycolipids, a substance which increases the intracellular, extracellular or serum level of a naturally occurring β-glycolipid, and any combination of the above (b) antigens associated with said immune-related disorder (c) at least one of liver-associated cells of tolerized or non-tolerized subjects suffering from said immune-related disorder or of said subject (d) at least one of cytokines, adhesion molecules or any combination thereof (e) antigen presenting cells and (f a combination of any of (a), (b), (c), (d) and (e).

According to another preferred embodiment, the therapeutic composition of the invention may comprise as an active ingredient, educated NK T cells capable of modulating the Th1/Th2 cell balance. More specifically, the educated NK T cells comprised within the composition of the invention were cultured in the presence of any one of: (a) a β-glycolipid, a mixture of at least two β-glycolipids, a substance which increases the intracellular, extracellular or serum level of a naturally occurring β-glycolipid, or any combination thereof; (b) antigens associated with said immune-related disorder (c) at least one of liver-associated cells of tolerized or non-tolerized subjects suffering from said immune-related disorder or of said subject (d) at least one of cytokines, adhesion molecules and any combination thereof (e) antigen presenting cells, and (f) a combination of any of (a), (b), (c), (d) and (e).

In a further aspect the invention relates to a method for the preparation of a medicament for the treatment of an immune related disorder in a subject in need thereof. The method of the invention may comprise the following steps: (a) obtaining a component of the immune system of said subject from said subject, or from another subject; and (b) ex vivo exposing by culturing or incubating said component obtained in step (a) with an effective amount of any one of a β-glycolipid, a mixture of at least two β-glycolipids, a substance which increases the intracellular, extracellular or serum level of a naturally occurring β-glycolipid, or any combination thereof, such that the resulting component has the capability of modulating the Th1/Th2 cell balance toward anti-inflammatory cytokine producing cells.

DETAILED DESCRIPTION OF THE INVENTION

Figure 1:
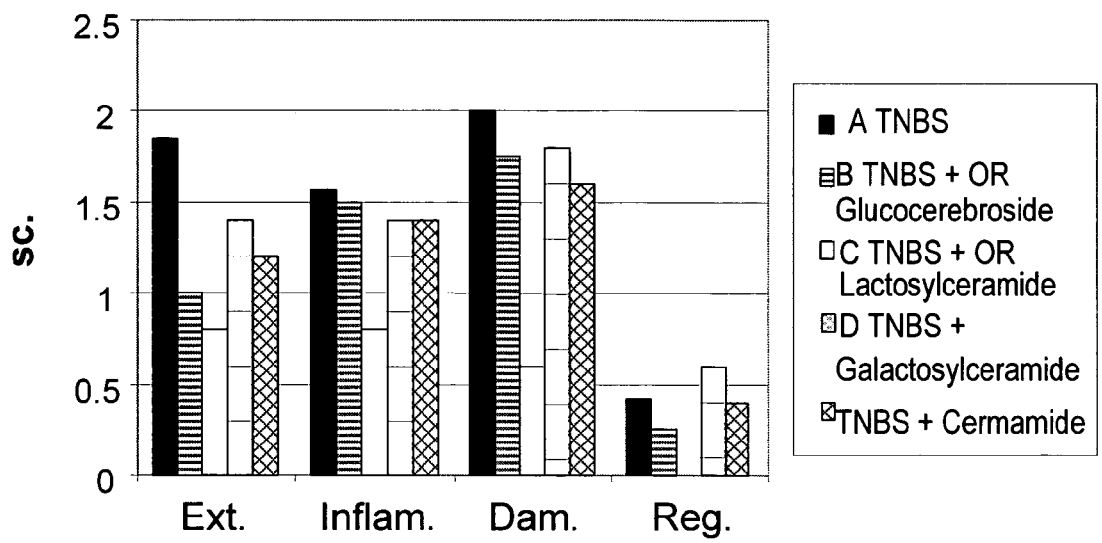
FIG. 1—Effect of glycolipids on pathology score. Abbreviations: sc. (score), Ext. (Extent), Inflam. (inflammation), Dam. (damage), Reg. (regeneration), OR (oral).

As a first aspect, the present invention relates to a process for the modulation of the Th1/Th2 cell balance toward anti-inflammatory cytokine producing cells, in a subject suffering from an immune related disorder. This process comprises the step of increasing the intracellular, extra-cellular or serum level of a naturally occurring β-glycolipid in a subject in need thereof. It should be noted that the modulation may be mediated by at least one component of said subject immune system. According to this embodiment, increasing the intracellular, extra-cellular or serum level of a naturally occurring β-glycolipid in said subject may be performed by:

(I). administering an effective amount of any one of: a β-glycolipid; a mixture of at least two β-glycolipids; a substance which increases the intracellular, extracellular or serum level of a naturally occurring β-glycolipid; and any combination of the above; or (II). exposing at least one component of said subject immune system to an effective amount of any one of: a β-glycolipid; a mixture of at least two β-glycolipids; a substance which increases the intracellular, extracellular or serum level of a naturally occurring β-glycolipid; and any combination of the above; or (III). any combination of (I) and (II) as indicated above.

According to one embodiment, a substance which increases the intracellular, extracellular or serum level of a naturally occurring β-glycolipid, may increase the rate of production of said β-glycolipid in said subject, or decrease the rate of degradation or turnover of said β-glycolipid in said subject.

According to another preferred embodiment the β-glycolipid used by the process of the invention may be selected from the group consisting of a monosaccharide ceramide, a glucosylceramide, a galatosylceremide, a lactosyl-ceramide, a gal-gal-glucosyl-ceramide, GM2 ganglioside, GM3 ganglioside, globoside or any other β-glycolipid. Preferably, the β-glycolipid used by the process of the invention may be β-lactosyl-ceramide and any analogue or derivative thereof. It should be appreciated that a process using a β-glycolipid other than glucosylceramide is also contemplated within the scope of the invention. Therefore, according to a particular embodiment, the process of the invention, wherein said β-glycolipid is any β-glycolipid other than glucosylceramide.

In yet another preferred embodiment, a mixture of β-glycolipids used by the process of the invention may comprise at least two β-glycolipids at a quantitative ratio between 1:1 to 1:1000. It should be appreciated that any quantitative ratio may be used. As a non-limiting example, a quantitative ratio used may be: 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, 1:100, 1:200, 1:300, 1:400, 1500, 1:750, 1:1000. It should be further noted that where the mixture of the invention comprises more than two glycolipids, the quantitative ratio used may be for example, 1:1:1, 1:2:3, 1:10:100, 1:10:100:1000 etc.

According to a specifically preferred embodiment, a mixture of preferred β-glycolipids used by the process of the invention comprises β-lactosyl-ceramide and at least one other β-glycolipid at a quantitative ratio between 1:1 to 1:1000. More preferably, such mixture comprises β-glucosylceramide and β-lactosyl-ceramide at a quantitative ratio between 1:1 to 1:1000.

As indicated herein before, the process of modulation of the Th1/Th2 cell balance toward anti-inflammatory cytokine may be mediated by at least one component of the subject immune system. According to a preferred embodiment, such component may be selected from the group consisting of cellular immune reaction elements, humoral immune reaction elements and cytokines. Preferably, such component may be a cellular immune reaction element.

According to a particular embodiment, the cellular immune reaction element may be a population of NK T cells. NK T cells can be obtained from bone marrow, liver, spleen, or uterus, but can also be obtained from the peripheral blood, by cytopheresis methods.

Thus, according to a specifically preferred embodiment, increasing the intracellular, extra-cellular or serum level of a naturally occurring β-glycolipid by the process of the invention, may be performed by exposing at least one component of said subject immune system, preferably, NK T cells to an effective amount of any one of a β-glycolipid, a mixture of at least two β-glycolipids, a substance which increases the intracellular, extracellular or serum level of a naturally occurring β-glycolipid and any combination of the above.

According to this specifically preferred embodiment, the process of the invention is performed by the steps of: (a) obtaining NK T cells from said subject, or from another subject; (b) ex vivo educating the NK T cells obtained in step (a) such that the resulting educated NK T cells have the capability of modulating the Th1/Th2 cell balance toward anti-inflammatory cytokine producing cells; and (c) re-introducing to said subject the educated NK T cells obtained in step (b) which are capable of modulating the Th1/Th2 cell balance toward anti-inflammatory cytokine producing cells, resulting in an increase in the quantitative ratio between any one of IL4 and IL10 to INFγ.

More particularly, ex vivo educating the NK T of step (b) may be performed by culturing said NK T cells in the presence of any one of: (a) a β-glycolipid, a mixture of at least two β-glycolipids, a substance which increases the intracellular, extracellular or serum level of a naturally occurring β-glycolipid, and any combination thereof; (b) antigens associated with said immune-related disorder or any combination thereof; (c) at least one of liver-associated cells of tolerized or non-tolerized subjects suffering from said immune-related disorder or of said subject; (d) at least one of cytokines, adhesion molecules or any combination thereof; (e) antigen presenting cells; and (f) a combination of any of (a), (b), (c), (d) and (e).

According to one embodiment, the NK T cell may be exposed to antigens associated with said immune-related disorder to be treated. These antigens may be for example, any one of allogeneic antigens obtained from a donor subject suffering from said immune-related disorder, xenogenic antigens, syngeneic antigens, autologous antigens, non-autologous antigens and recombinantly prepared antigens and any combinations thereof. These antigens can be native or non-native with regards to the subject. They can be natural or synthetic, modified or unmodified, whole or fragments thereof. Fragments can be derived from synthesis as fragments or by digestion or other means of modification to create fragments from larger entities. Such antigen or antigens comprise but are not limited to proteins, glycoproteins, enzymes, antibodies, histocompatibility determinants, ligands, receptors, hormones, cytokines, cell membranes, cell components, viruses, viral components, viral vectors, non-viral vectors, whole cells, tissues or organs. The antigen can consist of single molecules or mixtures of diverse individual molecules. The antigen can present itself within the context of viral surface, cellular surface, membrane, matrix, or complex or conjugated with a receptor, ligand, antibody or any other binding partner.

Polymerization and degradation, fractionation and chemical modification are all capable of altering the properties of a particular antigen in terms of potential immune responses. These small segments, fragments or epitopes can either be isolated or synthesized.

The method of the present invention further encompasses recombinantly prepared antigens. Preparation of recombinant antigens involves the use of general molecular biology techniques that are well known in the art. Such techniques include for example, cloning of a desired antigen to a suitable expression vector.

The liver was shown to play a role in T cell differentiation. $CD3^-CD4^+/CD8^+TCR\beta$ cells and $CD3$-4-$TCR\beta^+$ cells can be generated from $CD4^-8^-$-$TCR\beta$ athymic nude bone marrow cells by culture with liver parenchymal cells [Mabuchi, A., et al., J. Leukocyte Biology, 63:575-583 (1998)]. Therefore, in another particular embodiment, the ex vivo education of the NK T cells may be performed by culturing these cells in the presence of liver-associated cells. These cells may be for example Kupffer cells, Stellate cells, liver endothelial cells liver associated stem cells or any other liver-related lymphocytes.

Co-culturing of the NK T cells in the presence of peripheral lymphocytes from tolerized or non-tolerized patients suffering from the same immune-related disorder or from the treated subject, is also contemplated in the present invention. In order to obtain lymphocytes from a subject, particularly human subject, blood is drawn from the patient by cytopheresis, a procedure by which a large number of white cells are obtained, while other blood components are being simultaneously transferred back to the subject.

According to another embodiment, the NK T cell may be exposed to an antigen presenting cell that may be a dendritic cell.

In another particular embodiment, the ex-vivo education of the NK T cells may be performed by culturing the cells in the presence of cytokines such as IL4, IL10, TGFβ, INFγ, IL12 and IL15, or in the presence of adhesion molecules such as Integrins, Selectin and ICAM. In a specifically preferred embodiment, the NK T cell that has been ex vivo educated as described above may be re-introduced to the treated subject. This can be carried out by a process that has been termed adoptive transfer. The particular educated NK T cells used for the transfer may preferably originate from the subject (autologous transfer). A syngeneic or non-syngeneic donor (non-autologous transfer) is not excluded. The storage, growth or expansion of the transferred cells may have taken place in vivo, ex vivo or in vitro.

Cell therapy may be by injection, e.g., intravenously, or by any of the means described herein above. Neither the time nor the mode of administration is a limitation on the present invention. Cell therapy regimens may be readily adjusted taking into account such factors as the possible cytotoxicity of the educated cells, the stage of the disease and the condition of the patient, among other considerations known to those of skill in the art.

According to another embodiment, in addition to introducing to the treated subject ex vivo educated NK T cells, the process of the invention may further comprise the step of administering to said subject: (a) a β-glycolipid, a mixture of at least two β-glycolipids, a substance which increases the intracellular, extracellular or serum level of a naturally occurring β-glycolipid, and any combination thereof; (b) components, cells, tissues and/or organs derived from any one of allogeneic donors suffering from said immune-related disorder, xenogeneic sources and autologous sources, and immunologically functional equivalents, and combinations thereof; and (c) any combination of the above.

It is to be appreciated that the NK T cells may be educated in vivo as well, via any of the methods described above, they can be modulated prior to or at any point of time following exposure to the β-glycolipids, antigens or any other component described.

According to a specifically preferred embodiment, modulation of the Th1/Th2 cell balance toward anti-inflammatory cytokine producing cells, by the process of the invention may be performed by administering an effective amount of any one of: a β-glycolipid, a mixture of at least two β-glycolipids, a substance which increases the intracellular, extracellular or serum level of a naturally occurring β-glycolipid and any combination of the above. According to this embodiment, the administering step comprises oral, intravenous, intramuscular, subcutaneous, intraperitoneal, perenteral, transdermal, intravaginal, intranasal, mucosal, sublingual, topical, rectal or subcutaneous administration, or any combination thereof.

In yet another preferred embodiment, the process of the invention is particularly intended for modulation of the Th1/Th2 cell balance, in a subject suffering from an immune related disorder. According to this specific embodiment, the immune-related disorder may be any one of an autoimmune disease, malignant and non-malignant proliferative disorder, graft rejection pathology, inflammatory disease, genetic disease, bacterial infections, viral infections, fungal infections, or parasitic infections.

According to a specific embodiment, the malignant proliferative disorder may be any one of solid and non-solid tumor selected from the group consisting of carcinoma, sarcoma, melanoma, leukemia and lymphoma. More particularly, the malignant disorder may be melanoma, hepaotcellular carcinoma, colon cancer, myeloma, acute or chronic leukemia.

In yet another embodiment, the autoimmune disease may be any one of rheumatoid arthritis, diabetes, acute and chronic graft versus host disease, systemic lupus erythmatosus, scleroderma, multiple sclerosis, non alcoholic fatty liver disease, hyperlipidemia, atherosclerosis, the metabolic syndrome or any of the diseases comprising the same, obesity, inflammatory bowel disease and immune mediated hepatitis.

According to one specific embodiment, the process of the invention is particularly intended for modulation of the Th1/Th2 cell balance, in a subject suffering from diabetes.

According to another specific embodiment, the process of the invention is particularly intended for modulation of the Th1/Th2 cell balance, in a subject suffering from non alcoholic fatty liver disease.

According to another specific embodiment, the process of the invention is particularly intended for modulation of the Th1/Th2 cell balance, in a subject suffering from hyperlipidemia.

According to another specific embodiment, the process of the invention is particularly intended for modulation of the Th1/Th2 cell balance, in a subject suffering from the metabolic syndrome or any of the diseases comprising the same.

According to another specific embodiment, the process of the invention is particularly intended for modulation of the Th1/Th2 cell balance, in a subject suffering from obesity.

According to another specific embodiment, the process of the invention is particularly intended for modulation of the Th1/Th2 cell balance, in a subject suffering from inflammatory bowel disease.

According to another specific embodiment, the process of the invention is particularly intended for modulation of the Th1/Th2 cell balance, in a subject suffering from immune mediated, viral or chemical mediated hepatitis.

According to a particular embodiment, the viral infection comprises HBV, HCV or HIV.

In a second aspect, the invention relates to a method for the treatment of immune-related disorder in a mammalian subject in need thereof. According to one embodiment, the method of treatment comprises the step of administering to said subject an effective amount of any one of β-glycolipids, a mixture of at least two naturally occurring β-glycolipids and a substance which increases the intracellular, extracellular or serum level of a naturally occurring β-glycolipid, and of a composition comprising the same.

The invention further provides a method for the treatment of immune-related disorder in a mammalian subject in need thereof. According to this preferred embodiment, the method of the invention comprises the step of increasing the intracellular, extra-cellular or serum level of a naturally occurring β-glycolipid in said subject, by exposing at least one component of said subject immune-system to an effective amount of any one of: (a) a β-glycolipid; (b) a mixture of at least two β-glycolipids; (c) a substance which increases the intracellular, extracellular or serum level of a naturally occurring β-glycolipid; and (d) any combination of the above.

According to one embodiment, the substance which increases the intracellular, extracellular or serum level of a naturally occurring β-glycolipid, may increase the rate of production of said β-glycolipid in said subject, or decrease the rate of degradation or turnover of said β-glycolipid in said subject.

According to another preferred embodiment the β-glycolipid used by the method of the invention may be selected from the group consisting of a monosaccharide ceramide, a glucosylceramide, a galatosylceremide, a lactosyl-ceramide, a gal-gal-glucosyl-ceramide, GM2 ganglioside, GM3 ganglioside, globoside or any other β-glycolipid. Preferably, the β-glycolipid used by the process of the invention may be β-lactosyl-ceramide and any analogue or derivative thereof. A particular embodiment of this aspect relates to the use of a β-glycolipid other then glucosylceramide, for the method of the invention.

In yet another preferred embodiment, a mixture of β-glycolipids used by the method of the invention may comprise at least two β-glycolipids at a quantitative ratio between 1:1 to 1:1000. It should be appreciated that any quantitative ratio may be used. For example: 1:2, 1:50, 1:200, 1:350.

According to a specifically preferred embodiment, a mixture of preferred β-glycolipids used by the method of the invention may comprise β-lactosyl-ceramide and at least one other β-glycolipid at a quantitative ratio between 1:1 to 1:1000. More preferably, such mixture comprises β-glucosylceramide and β-lactosyl-ceramide at a quantitative ratio between 1:1 to 1:1000.

According to one preferred embodiment, the method of treatment may be based on exposing a component of the treated subject's immune system to the different β-glycolipids. According to a preferred embodiment, such component may be selected from the group consisting of cellular immune reaction elements, humoral immune reaction elements and cytokines. Preferably, such component may be a cellular immune reaction element.

According to a particular embodiment, the cellular immune reaction element may be a population of NK T cells.

More specifically, exposing NK T cells to an effective amount of the β-glycolipids of the invention may be performed by the steps of: (a). obtaining NK T cells from said subject, or from another subject; (b). ex vivo educating the NK T cells obtained in step (a) such that the resulting educated NK T cells have the capability of modulating the Th1/Th2 cell balance toward anti-inflammatory cytokine producing cells; and (c). re-introducing to said subject the educated NK T cells obtained in step (b) which are capable of modulating the Th1/Th2 cell balance toward anti-inflammatory cytokine producing cells, resulting in an increase in the quantitative ratio between any one of IL4 and IL10 to INFγ.

More particularly, ex vivo educating the NK T of step (b) may be performed by culturing said NK T cells in the presence of any one of: (a) a β-glycolipid, a mixture of at least two β-glycolipids, a substance which increases the intracellular, extracellular or serum level of a naturally occurring β-glycolipid, and any combination thereof; (b) antigens associated with said immune-related disorder or any combination thereof; (c) at least one of liver-associated cells of tolerized or non-tolerized subjects suffering from said immune-related disorder or of said subject; (d) at least one of cytokines, adhesion molecules or any combination thereof; (e) antigen presenting cells; and (f a combination of any of (a), (b), (c), (d) and (e).

According to one embodiment, the NK T cell may be exposed to antigens associated with said immune-related disorder. Such antigens may be for example, any one of allogeneic antigens obtained from a donor subject suffering from said immune-related disorder, xenogenic antigens, syngeneic antigens, autologous antigens, non-autologous antigens and recombinantly prepared antigens and any combinations thereof.

According to another embodiment, the NK T cell may be exposed to liver-associated cells which may be selected from the group consisting of Kupffer cells, Stellate cells, liver endothelial cells, liver-associated stem cells and any other liver-related lymphocytes.

In yet another embodiment, the NK T cell may be exposed to cytokines such as IL4, IL10, TGFβ, INFγ, IL12, IL2, IL18 and IL15.

Still further, the NK T cell may be exposed to adhesion molecules selected from the group consisting of Integrins, Selectin and ICAM.

According to another embodiment, the NK T cell may be exposed to an antigen presenting cell that may be a dendritic cell.

In a specifically preferred embodiment, the educated NK T cells may be re-introduced to the treated subject by adoptive transfer.

According to another embodiment, in addition to introducing to the treated subject ex vivo educated NK T cells, the method of the invention may further comprise the step of administering to said subject: (a) a β-glycolipid, a mixture of at least two β-glycolipids, a substance which increases the intracellular, extracellular or serum level of a naturally occurring β-glycolipid, and any combination thereof (b) components, cells, tissues and/or organs derived from any one of allogeneic donors suffering from said immune-related disorder, xenogeneic sources and autologous sources, and immunologically functional equivalents, and combinations thereof; and (c) any combination of the above.

According to another embodiment, the method of the invention comprises administering to the treated subject an effective amount of any one of: a β-glycolipid, a mixture of at least two β-glycolipids, a substance which increases the intracellular, extracellular or serum level of a naturally occurring β-glycolipid and any combination of the above. According to this embodiment, the administering step comprises oral, intravenous, intramuscular, subcutaneous, intraperitoneal, perenteral, transdermal, intravaginal, intranasal, mucosal, sublingual, topical, rectal or subcutaneous administration, or any combination thereof.

Therapeutic formulations may be administered in any conventional dosage formulation. Formulations typically comprise at least one active ingredient, as defined above, together with one or more acceptable carriers thereof.

Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. The nature, availability and sources, and the administration of all such compounds including the effective amounts necessary to produce desirable effects in a subject are well known in the art and need not be further described herein.

According to one preferred embodiment, the method of the invention is intended for the treatment of immune disorder such as autoimmune disease, malignant and non-malignant proliferative disorder, graft rejection pathology, inflammatory disease, genetic disease, bacterial infections, viral infections, fungal infections, or parasitic infections.

In another specifically preferred embodiment, the method of the invention is intended for the treatment of a malignancy. In cancerous situations, modulation of the NK T cells may be in the direction of inducing a pro-inflammatory response or in augmenting the anti-tumor associated antigens immunity. As used herein to describe the present invention, "cancer", "tumor" and "malignancy" all relate equivalently to a hyperplasia of a tissue or organ. If the tissue is a part of the lymphatic or immune systems, malignant cells may include non-solid tumors of circulating cells. Malignancies of other tissues or organs may produce solid tumors. In general, the methods and compositions of the present invention may be used in the treatment of non-solid and solid tumors.

Malignancy, as contemplated in the present invention may be selected from the group consisting of melanomas, carcinomas, lymphomas and sarcomas. Malignancies that may find utility in the present invention can comprise but are not limited to hematological malignancies (including leukemia, lymphoma and myeloproliferative disorders), hypoplastic and aplastic anemia (both virally induced and idiopathic), myelodysplastic syndromes, all types of paraneoplastic syndromes (both immune mediated and idiopathic) and solid tumors (including lung, liver, breast, colon, prostate GI tract, pancreas and Karposi). More particularly, the malignant disorder may be melanoma, hepaotcellular carcinoma, colon cancer, myeloma, acute or chronic leukemia.

In yet another embodiment, the autoimmune disease may be any one of rheumatoid arthritis, diabetes, acute and chronic graft versus host disease, systemic lupus erythmatosus, scleroderma, multiple sclerosis, non alcoholic fatty liver disease, hyperlipidemia, atherosclerosis, the metabolic syndrome or any of the diseases comprising the same, obesity, inflammatory bowel disease and immune mediated hepatitis.

According to a particular embodiment, the viral infection comprises HBV, HCV or HIV.

According to a specifically preferred embodiment, wherein the treated subject is suffering from any of the diseases indicated above, a preferred result of the treatment by the method of the invention may be for example, an increase in glucose tolerance, reduction in liver fat content or change in cytokine responses. Such results are demonstrated by the following examples.

According to one specific embodiment, the method of the invention is particularly intended for the treatment of a subject suffering from diabetes.

According to another specific embodiment, the method of the invention is particularly intended for the treatment of a subject suffering from non alcoholic fatty liver disease.

According to another specific embodiment, the method of the invention is particularly intended for the treatment of a subject suffering from hyperlipidemia.

According to another specific embodiment, the method of the invention is particularly intended for the treatment of a subject suffering from the metabolic syndrome or any of the diseases comprising the same.

According to another specific embodiment, the method of the invention is particularly intended for the treatment of a subject suffering from obesity.

According to another specific embodiment, the process of the invention is particularly intended for the treatment of a subject suffering from inflammatory bowel disease.

According to another specific embodiment, the method of the invention is particularly intended for the treatment of a subject suffering from immune mediated, viral or chemical mediated hepatitis.

Although the methods of the invention is particularly intended for the treatment of immune-related disorders in humans, other mammals are included. By way of non-limiting examples, mammalian subjects include monkeys, equines, cattle, canines, felines, mice, rats and pigs.

In a third aspect, the invention relates to a therapeutic composition for the treatment of an immune-related disorder in a mammalian subject. According to one embodiment, the composition of the invention may comprise as an active ingredient: (a) β-glycolipid; a mixture of at least two β-glycolipids a substance which increases the intracellular, extracellular or serum level of a naturally occurring β-glycolipid and any combination of the above (b) antigens associated with said immune-related disorder; (c) at least one of liver-associated cells of tolerized or non-tolerized subjects suffering from said immune-related disorder or of said subject; (d) at least one of cytokines, adhesion molecules or any combination thereof; (e) antigen presenting cells; and (f) a combination of any of (a), (b), (c), (d) and (e).

According to another preferred embodiment, the therapeutic composition of the invention may comprise as an active ingredient, educated NK T cells capable of modulating the Th1/Th2 cell balance toward anti-inflammatory cytokine producing cells. More specifically, the educated NK T cells comprised within the composition of the invention were cultured in the presence of any one of: (a) a β-glycolipid, a mixture of at least two β-glycolipids, a substance which increases the intracellular, extracellular or serum level of a naturally occurring β-glycolipid, or any combination thereof; (b) antigens associated with said immune-related disorder; (c) at least one of liver-associated cells of tolerized or non-tolerized subjects suffering from said immune-related disorder or of said subject; (d) at least one of cytokines, adhesion molecules and any combination thereof (e) antigen presenting cells; and (f a combination of any of (a), (b), (c), (d) and (e).

According to one embodiment, the substance which increases the intracellular, extracellular or serum level of a naturally occurring β-glycolipid; may be a substance which increases the rate of production of said β-glycolipid in said subject, or a substance which decreases the rate of degradation or turnover of said β-glycolipid in said subject.

According to another preferred embodiment the β-glycolipid comprised within the composition of the invention may be selected from the group consisting of a monosaccharide ceramide, a glucosylceramide, a galatosylceremide, a lactosyl-ceramide, a gal-gal-glucosyl-ceramide, GM2 ganglioside, GM3 ganglioside, globoside or any other β-glycolipid. Preferably, the β-glycolipid used by the process of the invention may be β-lactosyl-ceramide and any analogue or derivative thereof. Compositions comprising a β-glycolipid other than glucosylceramide are also within the scope of the invention.

In yet another preferred embodiment, a mixture of β-glycolipids used by the composition of the invention may comprise at least two β-glycolipids at a quantitative ratio between 1:1 to 1:1000. It should be appreciated that any quantitative ratio may be used.

According to a specifically preferred embodiment, a mixture of preferred β-glycolipids comprised within the composition of the invention may comprise β-lactosyl-ceramide and at least one other β-glycolipid at a quantitative ratio between 1:1 to 1:1000. More preferably, such mixture comprises β-glucosylceramide and β-lactosyl-ceramide at a quantitative ratio between 1:1 to 1:1000.

According to one preferred embodiment, the composition of the invention comprises ex vivo educated NKT cells. These cells were exposed to antigens associated with the immune-related disorder to be treated. Such antigens may for example, allogeneic antigens obtained from a donor subject suffering from said immune-related disorders, xenogenic antigens, syngeneic antigens, autologous antigens, non-autologous antigens and recombinantly prepared antigens and any combinations thereof.

According to one embodiment, the NK T cell may be exposed to antigens associated with said immune-related disorder. Such antigens may be for example, any one of allogeneic antigens obtained from a donor subject suffering from said immune-related disorder, xenogenic antigens, syngeneic antigens, autologous antigens, non-autologous antigens and recombinantly prepared antigens and any combinations thereof.

According to another embodiment, the NK T cell may be exposed to liver-associated cells which may be selected from the group consisting of Kupffer cells, Stellate cells, liver endothelial cells, liver-associated stem cells and any other liver-related lymphocytes.

In yet another embodiment, the NK T cell may be exposed to cytokines such as IL4, IL10, TGFβ, INFγ, IL12, IL2, IL18 and IL15.

Still further, the NK T cell may be exposed to adhesion molecules selected from the group consisting of Integrins, Selectin and ICAM.

According to another embodiment, the NK T cell may be exposed to an antigen presenting cell that may be a dendritic cell.

According to one embodiment, the composition of the invention is intended for the treatment of an immune disorder such as an autoimmune disease, malignant and non-malignant proliferative disorder, graft rejection pathology, inflammatory disease, genetic disease, bacterial infections, viral infections, fungal infections, or parasitic infections.

According to a specific embodiment, the malignant proliferative disorder may be any one of solid and non-solid tumor selected from the group consisting of carcinoma, sarcoma, melanoma, leukemia and lymphoma. More particularly, the malignant disorder may be melanoma, hepaotcellular carcinoma, colon cancer, myeloma, acute or chronic leukemia.

In yet another embodiment, the autoimmune disease may be any one of rheumatoid arthritis, diabetes, acute and chronic graft versus host disease, systemic lupus erythmatosus, scleroderma, multiple sclerosis, non alcoholic fatty liver disease, hyperlipidemia, atherosclerosis, the metabolic syndrome or any of the diseases comprising the same, obesity, inflammatory bowel disease and immune mediated hepatitis.

It should be noted that the composition of the invention is particularly suitable for the treatment of diabetes.

According to another specific embodiment, the composition of the invention is particularly intended for the treatment of a subject suffering from non alcoholic fatty liver disease.

According to another specific embodiment, the composition of the invention is particularly intended for the treatment of a subject suffering from hyperlipidemia.

According to another specific embodiment, the composition of the invention is particularly intended for the treatment of a subject suffering from the metabolic syndrome or any of the diseases comprising the same.

According to another specific embodiment, the composition of the invention is particularly intended for the treatment of a subject suffering from obesity.

According to another specific embodiment, the composition of the invention is particularly intended for the treatment of a subject suffering from inflammatory bowel disease.

According to another specific embodiment, the composition of the invention is particularly intended for the treatment of a subject suffering from immune mediated, viral or chemical mediated hepatitis.

According to a particular embodiment, the viral infection comprises HBV, HCV or HIV.

The pharmaceutical compositions of the invention generally comprise a buffering agent, an agent which adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

In a further aspect the invention relates to a method for the preparation of a medicament for the treatment of an immune related disorder in a subject in need thereof. The method of the invention may comprise the following steps: (a) obtaining a component of the immune system of said subject from said subject, or from another subject; and (b) ex vivo exposing by culturing or incubating said component obtained in step (a) with an effective amount of any one of a β-glycolipid, a mixture of at least two β-glycolipids, a substance which increases the intracellular, extracellular or serum level of a naturally occurring β-glycolipid, or any combination thereof, such that the resulting component has the capability of modulating the Th1/Th2 cell balance toward anti-inflammatory cytokine producing cells.

According to one embodiment, the component of said subject immune system may be a cellular immune reaction element. More specifically, a population of NK T cells.

According to a specifically preferred embodiment, the method of the invention may be performed by the steps of: (a) obtaining NK T cells from said subject, or from another subject; and (b) ex vivo educating the NK T cells obtained in step (a) by culturing said NK T cells in the presence of any one of: (i) a β-glycolipid, a mixture of β-glycolipids, a substance which increases the intracellular, extracellular or serum level of a naturally occurring β-glycolipid, or any combination thereof; (ii) antigens associated with said immune-related disorder or any combination thereof; (iii) at least one of liver-associated cells of tolerized or non-tolerized subjects suffering from said immune-related disorder or of said subject; (iv) at least one of cytokines, adhesion molecules or any combination thereof; (v) antigen presenting cells; and (vi) a combination of any of (a), (b), (c), (d) and (e);

According to this preferred embodiment, the resulting educated NK T cells have the capability of modulating the Th1/Th2 cell balance toward anti-inflammatory cytokine producing cells.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

Animals

Normal inbred 2 to 4 month old C57B1 male mice were obtained from Jackson Laboratories, USA.

Normal inbred 2 to 4 month old Balb/C male mice were obtained from Jackson Laboratories, USA.

Ten-week-old male leptin-deficient C57BL/6J mice and lean C57BL/6 mice were purchased from Harlan laboratories.

All animals were maintained in the Animal Core of the Hadassah-Hebrew University Medical School. Mice were maintained on standard laboratory chow and kept in 12-hour light/dark cycles.

β-Glycolipids

The following β-glycolipids were used: β-glucosylceramide (GluC), β-lactosyl-ceramide (LacC), and β-galactosyl-ceramide (GalC) and ceramid Induction of Colitis 2,4,6-trinitrobenzene sulfonic acid (TNBS)—colitis was induced by intracolonic instillation of TNBS, 1 mg/mouse, dissolved in 100 ml of 50% ethanol as described. [Collins, C., et al., Eur. J. Immunol. 26:3114-3118 (1996)].

Clinical Assessment of Colitis

Diarrhea was followed daily throughout the study.

Macroscopic Score of Colitis

Colitis assessment was performed 14 days following colitis induction using standard parameters [Madsen, K. L., et al., Gastroenterology 113:151-159 (1997); Trop, S., et al., Hepatology 27:746-755 (1999)].

Four macroscopic parameters were determined, namely: degree of colonic ulcerations; intestinal and peritoneal adhesions; wall thickness; and degree of mucosal edema. Each parameter was graded on a scale from 0 (completely normal) to 4 (most severe) by two experienced blinded examiners.

Grading of Histological Lesions

For histological evaluation of inflammation, distal colonic tissue (last 10 cm) was removed and fixed in 10% formaldehyde. Five paraffin sections from each mouse were then stained with hematoxylin-eosin by using standard techniques. The degree of inflammation on microscopic cross sections of the colon was graded semiquantitatively from 0 to 4 [Madsen et al., (1997) ibid.; Trop et al., Hepatology 27:746-755 (1999)]. Grade 0: normal with no signs of inflammation; Grade 1: very low level of leukocyte infiltration; Grade 2: low level of leukocyte infiltration; and Grade 3: high level of infiltration with high vascular density, and bowel wall thickening; Grade 4: transmural infiltrates with loss of goblet cells, high vascular density, wall thickening, and disruption of normal bowel architecture. The grading was performed by two experienced blinded examiners.

Splenic and Hepatic Lymphocyte Isolation

Splenocytes were isolated and red blood cells removed as previously described [Vicari, A. P., et al., Immunology Today 17(2):71 (1996)]. Intrahepatic lymphocytes were isolated from all groups of mice at the end of the study, as previously described, with some modifications [Vicari et al., (1996) ibid.; Bleicher, P. A., et al., Science 250:679-682 (1990)]. The inferior vena cava was cut above the diaphragm and the liver was flushed with 5 ml of cold PBS until it became pale. The connective tissue and the gall bladder were removed, and livers were place in a 10-ml dish in cold sterile PBS. Livers and spleens were crushed through a stainless mesh (size 60, Sigma Chemical Co., St. Louis Mo.). Cell suspension was placed in a 50 ml tube for 3 minutes and washed twice in cold PBS (1,250×rpm for 10 minutes), and debris was removed. Cells were re-suspended in PBS, cell suspension was placed through a nylon mesh presoaked in PBS, and unbound cells were collected. Cells were washed twice in 45 ml PBS (1,250×rpm in room temperature). For liver and spleen lymphocyte isolation 20 ml of histopague 1077 (Sigma Diagnostics, St. Louis, Mo.) were slowly placed underneath the cells suspended in 7 ml of PBS, in a 50-ml tube. The tube was centrifuged at 1,640 rpm for 15 minutes at room temperature. Cells at the interface were collected, diluted in a 50-ml tube, and washed twice with ice-cold PBS (1,250 rpm for 10 minutes). Approximately $1 \times 10^6$ cells/mouse liver were recovered. The viability by trypan blue staining was more than 95%. Both splenocytes and liver-associated lymphocytes were isolated from all animals in all experimental groups.

FACS of Intrahepatic and Intrasplenic Lymphocytes for NKT, CD4 and CD8 Markers

Immediately following lymphocyte isolation, triplicates of $2-5 \times 10^4$ cells/500 µl PBS were put into Falcon 2052 tubes incubated with 4 ml of 1% BSA for 10 minutes, and centrifuged at 1400 rpm for 5 minutes. Analysis of lymphocyte subpopulations was performed using anti-NK1.1, anti-CD3, anti-CD4 and anti CD-8 antibodies. Cells were washed twice in 1% BSA, and kept in 4° C. until reading. For the control group, only 5 µl of 1% BSA was added. Analytical cell sorting was performed on $1 \times 10^4$ cells from each group with a fluorescence-activated cell sorter (FACSTAR plus, Becton Dickinson). Only live cells were counted, and background fluorescence from non-antibody-treated lymphocytes was deducted from the levels obtained. Gates were set on forward- and side-scatters to exclude dead cells and red blood cells.

The data were analyzed with Consort 30 two-color contour plot program (Becton Dickinson, Oxnard, Calif.), or the CELLQuest program.

Measurement of Cytokine Levels

Blood was drawn from mice in all groups and centrifuged at 14,000 rpm. Serum INFγ, IL2, IL4, IL10 and IL-12 levels were measured by "sandwich" ELISA using Genzyme Diagnostics kits (Genzyme Diagnostics, Mass.).

Glucose Tolerance Test

Glucose tolerance was assessed by oral administration of glucose (1 gram per kilogram body weight). Blood drawn from the tail was measured for glucose at 0', 15', 30', 60', 90', 120' and 180'. Glucose levels were measured with Elite glucose test strips and a glucometer.

Hepatic MRI Measurement of Fat Content

Hepatic fat content was measured using a double-echo chemical shift gradient-echo magnetic resonance imaging (MRI) sequence that provides in-phase and opposed-phase images in a single acquisition for assessment/quantification of fat in mouse liver. The T1-weighted opposed-phase MR imaging technique is sensitive for detection of relatively small amounts of tissue fat. MRI images were performed with a 1.5-T system (Signa LX; GE, Milwaukee, USA). Double-echo MR imaging was performed with a repetition time (TR) of 125 msec, double echo times (TEs) of 4 and 6.5 msec, and a flip angle of 80°. Imaging parameters included section thickness of 3 mm, 13-cm field of view, 256*160 matrix, and one signal acquired, with use of a knee coil. Transverse (axial) and coronal images were acquired at the level of the liver with a 3 mm section thickness and no intersection gap. Quantitative assessment of signal intensity (SI) measurements of SI changes between in-phase and opposed-phase images was computed as described in previous reports [Mitchell, D. G. et al., Invest. Radiol 26:1041-1052 (1991); Tomohiro, N. et al., Radiology 218:642-646 (2001)]. The SI index was calculated as follows: SI index=$(SI_{ip}-SI_{op})/SI_{ip}$, where $SI_{ip}$ is SI on in-phase images and $SI_{op}$ is SI on opposed-phase images. The SI index reflects the fraction of SI loss on opposed phase images compared with the SI on in-phase images.

Example 1

Use of β-Glycolipids for Treatment of Immune Mediated Colitis

To determine the clinical and immunological effect of administration of β-glycolipids such as β-glucosylceramide (GluC), β-lactosyl-ceramide (LacC), and β-galactosyl-ceramide (GalC) and of ceramide on a murine model of experimental colitis, nine groups of C57Bl mice, consisting of 10 mice each, were studied. As summarized in Table 1, colitis was induced by intracolonic installation of trinitrobenzene-sulfonic acid (TNBS) on day 1 and 5 in groups A-E. Group A mice were fed regular chow diet. Group B-E mice received oral (PO) 15 μg daily of GluC, LacC, GalC and ceramide, respectively. Groups F-I mice were not treated with TNBS, but received oral (PO) 15 μg daily of GluC, LacC, GalC and ceramide, respectively, and served as control groups.

Mice were followed for macroscopic and microscopic colitis scores. The immunemodulatory effect of GC was determined by FACS analysis of intrahepatic and intrasplenic lymphocytes for NKT, CD4 and CD8 markers, and by measurement of serum IFNγ, IL2, IL12, IL4 and IL10 cytokine levels.

TABLE 1

| Group: | Treatment: |
| --- | --- |
| A | TNBS |
| B | TNBS with OP 15 μg β-GluC |
| C | TNBS with OP 15 μg β-LacC |
| D | TNBS with OP 15 μg β-GalC |
| E | TNBS with OP 15 μg ceramide |
| F | OP 15 μg β-GluC |
| G | OP 15 μg β-LacC |
| H | OP 15 μg β-GalC |
| I | OP 15 μg ceramide |

Figure 2:
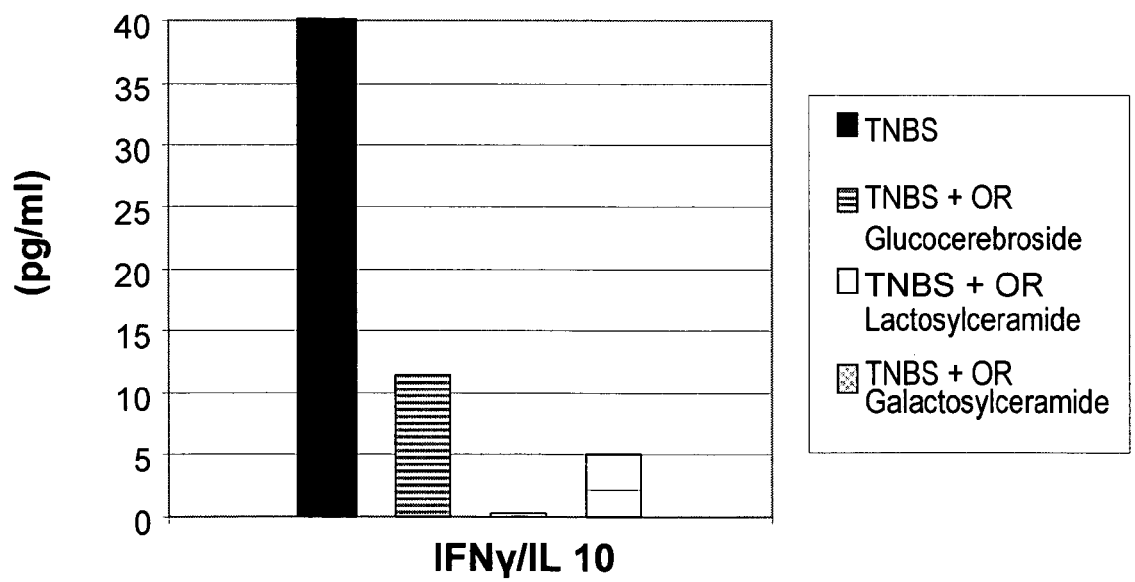
FIG. 2—Effect of glycolipids serum cytokine levels. Abbreviations: OR (oral), pg/ml (pictogram/milliliter).
Figure 3:
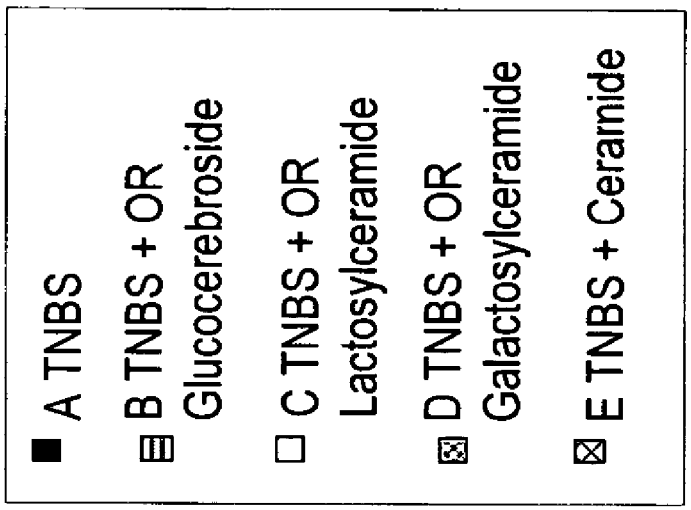
FIG. 3—Effect of glycolipids on T lymphocyte distribution. Abbreviations: OR (oral), Per. (peripheral), Liv. (liver), Rat. (ratio).
Figure 3:
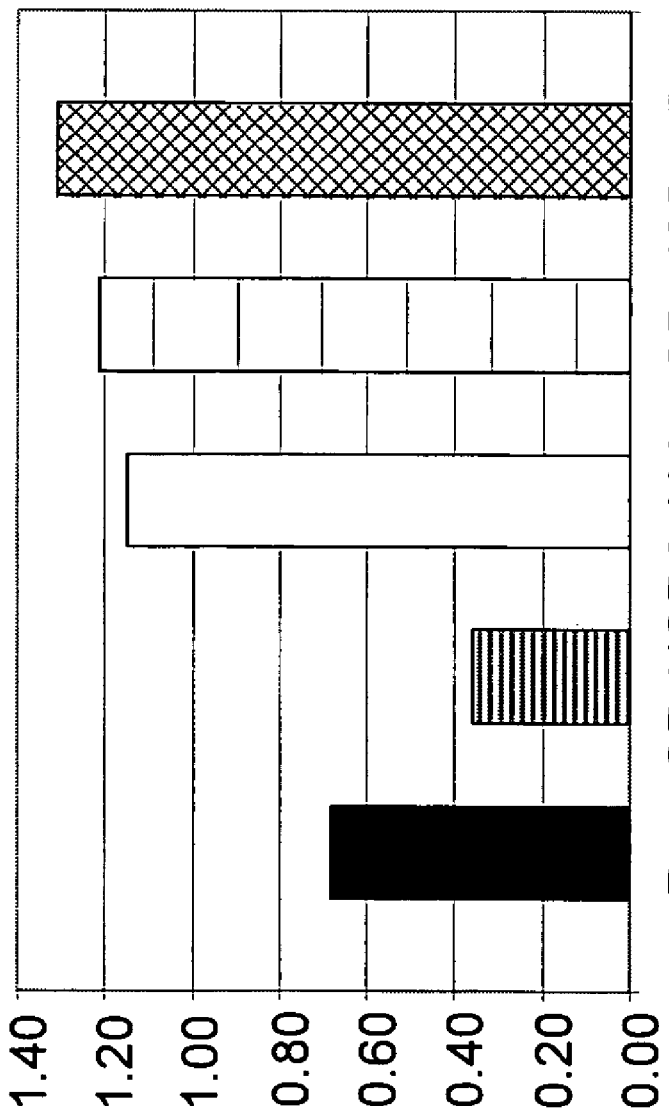

As shown in FIG. 1, administration of β-glycolipids resulted in alleviation of colitis, most marked for LacC, with improvement of the microscopic colitis scores as compared with controls. Alleviation of colitis by β-glycolipid treatment was associated with a significant increase of intrahepatic CD8+ T cell trapping (FIG. 3). The beneficial effect of β-glycolipids on TNBS colitis was associated with an increase in the number of intrahepatic NKT cells. As clearly shown in FIG. 2, administration of beta glycolipids led to a decreased serum INFγ level and decreased INFγ/IL-10 ratio. As was demonstrated by the control groups (F-I), administration of different β-glycolipids to naïve mice did not have adversely affect functional status, weight, liver and colon pathology.

The data clearly indicate that β-glycolipids alleviate experimental colitis in a murine model. This alleviation was accompanied by increased intrahepatic NKT lymphocytes, increased intrahepatic CD8 T lymphocyte trapping, and a shift toward a Th2 cytokine profile (as indicated by the reduced IFNγ/IL-10 ratio). The extent of this effect varies according to the different glycolipid used. Lactosyl-ceramide was found to be the most potent in this respect.

Example 2

Use of β-Glycolipids for the Treatment of Immune Hepatocelular Carcinoma

To determine the clinical and immunological consequences of administration of different β-glycolipids such as β-glucosylceramide (GluC), β-lactosyl-ceramide (LacC), and β-galactosyl-ceramide (GalC) and of ceramide on hepatocellular carcinoma (HCC), mice transplanted with human Hep3B HCC cells, were studied. Five groups of athymic Balb/c mice, consisting of 8 mice each, were sublethally irradiated and transplanted with human Hep3B HCC, followed by daily intraperitoneal injections of GluC, LacC, GalC, ceramide (1.5 μg in 100 μl PBS) or PBS (100μ) for 25 days. Animals were followed for tumor size and weight and for intrahepatic and intrasplenic lymphocyte subpopulations, serum cytokine levels and expression of STAT1, STAT4 and STAT6 in splenocytes. The different test groups are summarized in Table 2.

TABLE 2

| Group: | Treatment: |
| --- | --- |
| A | Hep3B HCC, 1.5 μg β-GluC |
| B | Hep3B HCC, 1.5 μg β-LacC |
| C | Hep3B HCC, 1.5 μg β-GalC |
| D | Hep3B HCC, 1.5 μg ceramide |
| E | Hep3B HCC, PBS control |

Figure 4:
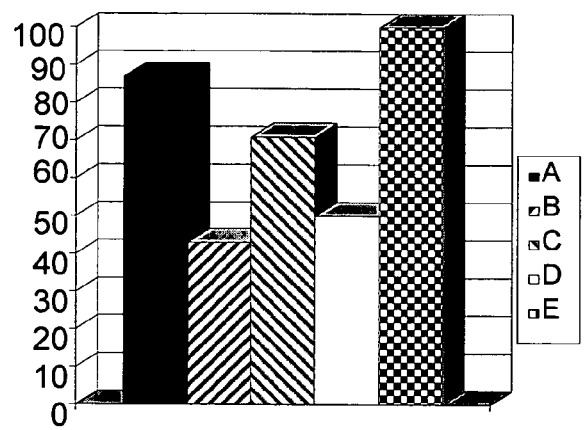
FIG. 4—Effect of glycolipids on tumor development (%).
Figure 5:
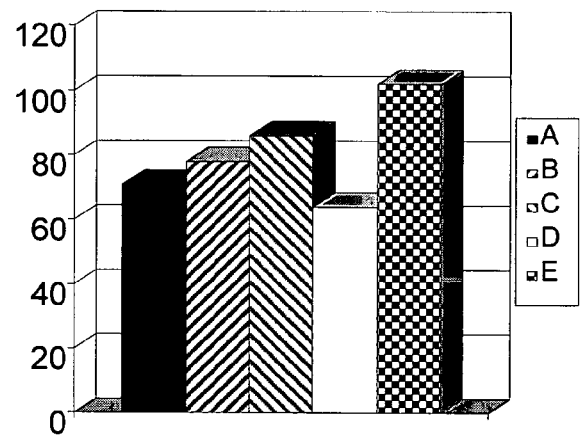
FIG. 5—Effect of glycolipids on maximal tumor volume ($mm^3$).
Figure 6:
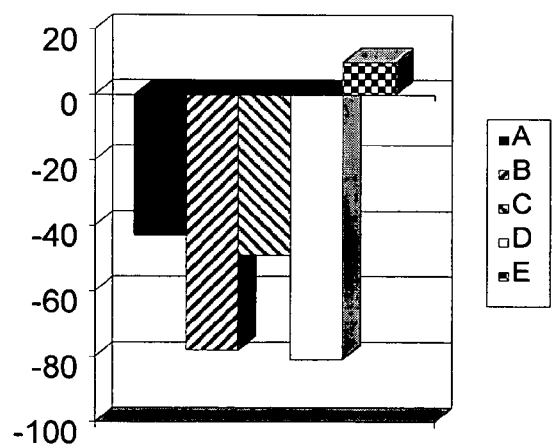
FIG. 6—Effect of glycolipids on tumor progression (% change from maximal volume).
Figure 7:
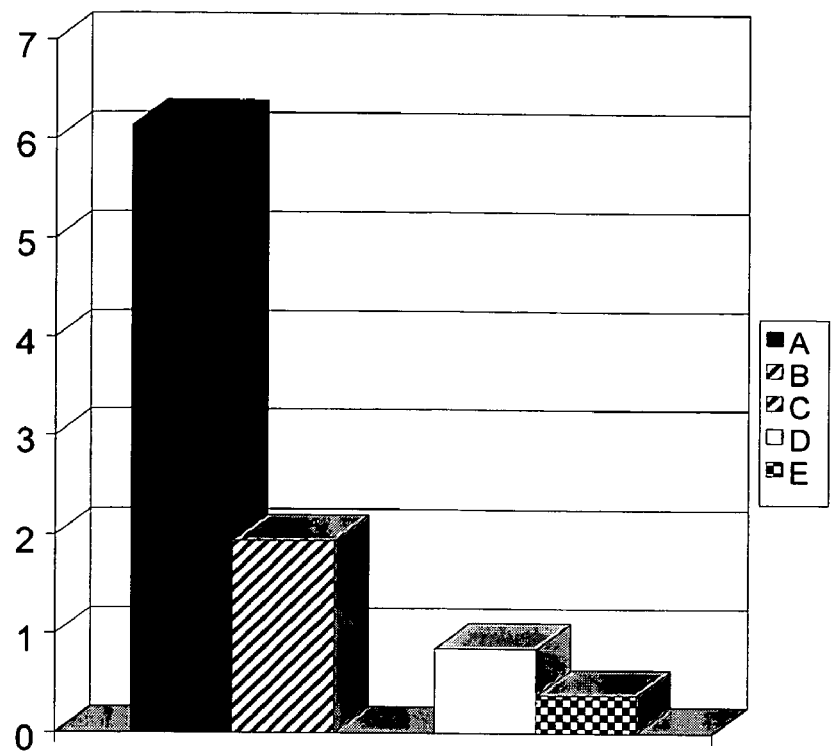
FIG. 7—Effect of glycolipids on hepatic/splenic NKT lymphocyte ratio.
Figure 8:
FIG. 8—Effect of glycolipids on intrahepatic CD8+ T lymphocyte trapping (spleen/liver CD4/CD8 ratio).
Figure 9:
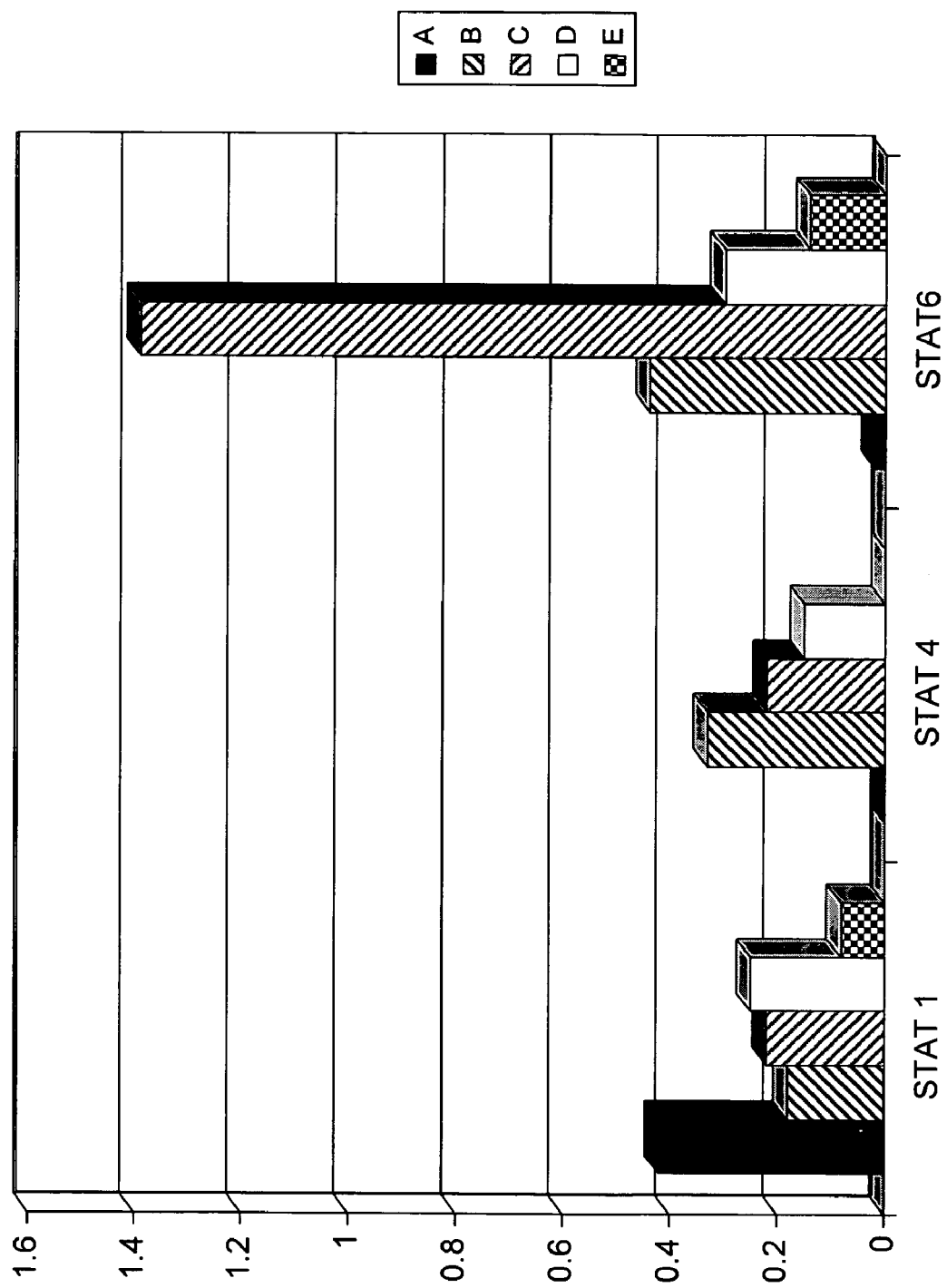
FIG. 9—Effect of glycolipids on STAT 1, STAT 4 and STAT 6 expression (ODx$mm^2$).

As shown in FIG. 4, administration of β-glycolipids and ceramide resulted in marked suppression of HCC. Tumors developed in 87%, 43%, 71% and 50% of GluC, LacC, GalC and ceramide-treated animals, respectively, compared to 100% of controls. FIG. 5 further shows that maximal tumor volume was 71.4, 77.9, 86.1 and 64.4 mm³ in GluC, LacC, GalC and ceramide-treated animals, respectively, compared to 101.14 mm³ in controls (p<0.05). Moreover, FIG. 6 indicates a 43%, 78%, 49% and 81% reduction of tumor volume, in GluC, LacC, GalC and ceramide treated mice, respectively, in contrast to a 10% increase in tumor volume in controls (p<0.05). Body weight did not differ significantly among the groups. As shown in FIG. 7, the beneficial effect of β-glycolipids was associated with increased intrahepatic NKT lymphocytes (hepatic/splenic NKT lymphocyte ratio 6.13, 1.94, 0.85 and 0.38 in groups A, B, D and E, respectively, p<0.05). FIG. 8 shows that the effect of β-glycolipids was further associated with increased intrahepatic CD8 T lymphocyte trapping. As shown in FIG. 9, STAT1 expression in splenocytes was increased in glycolipid-treated mice vs. controls; STAT4 and STAT6 expression were increased in LacC, GalC and ceramide-treated animals. It should be noted that serum cytokine levels did not differ significantly between the groups (data not shown).

These results clearly demonstrate the feasibility of using β-glycolipids for the treatment of HCC. Administration of β-glycolipids resulted in suppression of HCC, accompanied by increased intrahepatic NKT lymphocytes, increased intrahepatic CD8 T lymphocyte trapping and increased expression of STAT1, STAT4 and STAT6 in splenocytes. These results suggest that α configuration of glycolipid sugars may not be essential for NKT cell-related anti tumor effects.

Example 3

Synergistic Effect for Mixtures of β-Glycolipids in the Treatment of Immune Mediated Colitis To determine the possible immuno-modulation effect of a mixture of different β-glycolipids, the effect of a mixture of β-Glucocerebroside and β-Lactosyl-ceramide was tested using a murine model of colitis.

As summarized in Table 3, five groups of mice were studied, each consisting of 10 mice. Colitis was induced by intracolonic installation of trinitrobenzenesulfonic acid (TNBS) on day 1 and 5 in groups A, B and D. Group A mice were fed regular chow diet. Group B mice received oral (PO) 15 µg daily of a mixture of β-GluC and β-LacC, group D received only β-LacC. Groups C and E mice were not treated with TNBS, but received oral (PO) 15 µg daily of a mixture of β-GluC and β-LacC or only β-LacC, respectively, and served as control groups.

Mice were followed for macroscopic and microscopic colitis scores, as well as for survival and functional status and weight.

TABLE 3

| Group: | Treatment: |
|--------|------------|
| A | TNBS |
| B | TNBS with 15 µg β-GluC + 15 µg β-LacC |
| C | 15 mg β-GluC + 15 µg β-LacC |
| D | TNBS with 15 µg β-LacC |
| E | 15 µg β-LacC |

Figure 10:
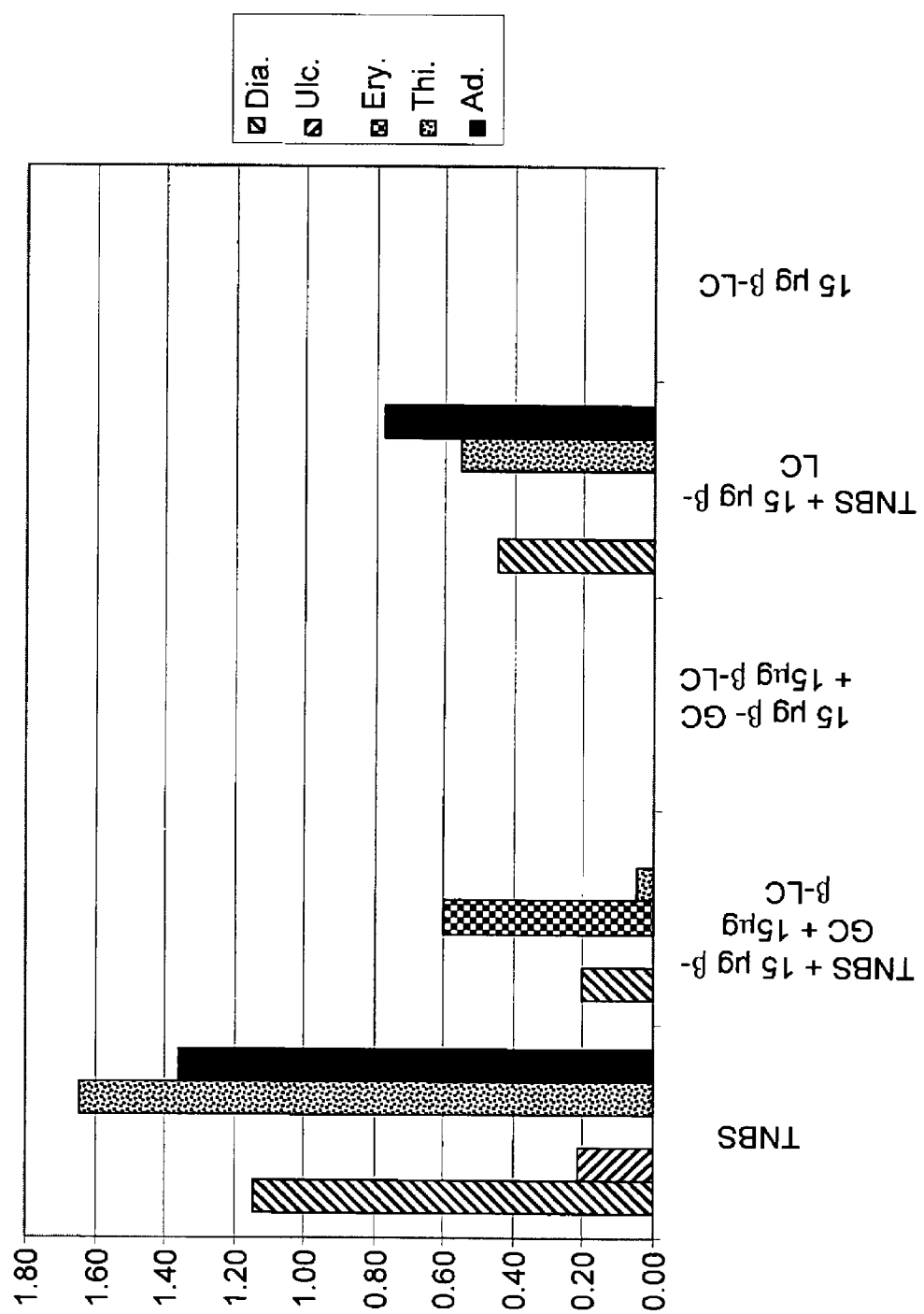
FIG. 10—Effect of combination treatment of macroscopic score of colitis. Abbreviations: Dia (diarrhea), Ulc. (ulcers), Ery. (erythema), Th. (thickness), Ad. (adhesion).

A clear synergistic effect of the β-GluC+β-LacC mixture is demonstrated by FIG. 10. As shown by this figure, administration of a mixture of both β-GlucC and β-LacC, led to significant amelioration of TNBS induced colitis, as indicated by the reduction in diarrhea, ulcers erythema, thickness and adhesions. This effect was much more significant in the β-GluC+β-LacC mixture group, when compared to the effect of β-LacC alone. As indicated by Table 4, the synergistic effect of the β-GluC+β-LacC mixture was further demonstrated by improved functional status, weight and 40% increase in survival.

TABLE 4

| Group | Activity | Weight |
|-------|----------|--------|
| TNBS | Lethargic | Weight loss |
| TNBS with 15 µg β-GC SOY + 15 µg β-LC | Normal | In 80% no change |
| | | In 20% increase |
| 15 µg β-GC SOY + 15 µg β-LC | Normal | In 100% increase |
| TNBS with 15 µg β-LC | Normal | In 90% no change |
| | | In 10% increase |
| 15 µg β-LC | Normal | In 100% increase |

Example 4

Mixed Glycolipids in Colitis

To test different combinations of the two most potent β-glycolipids, β-glucocerebroside and β-lactosyl-ceramide, and to identify the most effective mixture combination, different quantitative ratio of both glycolipids were used (1:1, 1:10, and 1:100), using a murine model of colitis.

As summarized in Table 4, seventeen groups of C57BL mice are studied, each consisting of 10 mice. Colitis is induced by intracolonic installation of trinitrobenzenesulfonic acid (TNBS) on day 1 and 5 in groups A, B, D, F, H, J, L, M, and N. Group A mice were fed regular chow diet. Groups B-K mice are receiving oral (PO) daily of a mixture of β-GluC and β-LacC in different ratio, as indicated by the table. Groups L-Q are receiving only β-LacC. Groups C, E, G, I, K, Q, O and P mice are not treated with TNBS, but are receiving oral mixture of β-GluC and β-LacC or only β-LacC, respectively, and serving as control groups.

Mice are followed for macroscopic and microscopic colitis scores, as well as for different cell populations by FACS: CD4, CD8, NKT (CD3+NK1.1, CD4+NK1.1, CD8+NK1.1) in spleen and liver (not pooled), and for serum cytokines by ELISA: INFγ, TGFβ, IL2, IL4, IL10, and IL12

TABLE 5

| Group | Day 1 and 5 | Day 1–9 feeding |
|-------|-------------|-----------------|
| A | TNBS 0.5 mg × 2 | — |
| B | TNBS 0.5 mg × 2 | 15 µg β-GC with 15 µg β-LC |
| C | — | 15 µg β-GC with 15 µg β-LC |
| D | TNBS 0.5 mg × 2 | 15 µg β-GC with 150 µg β-LC |
| E | — | 15 µg β-GC with 150 µg β-LC |
| F | TNBS 0.5 mg × 2 | 150 µg β-GC with 15 µg β-LC |
| G | — | 150 µg β-GC with 15 µg β-LC |
| H | TNBS 0.5 mg × 2 | 15 µg β-GC with 1500 µg β-LC |
| I | — | 15 µg β-GC with 1500 µg β-LC |
| J | TNBS 0.5 mg × 2 | 1500 µg β-GC SOY with 15 µg β-LC |
| K | — | 1500 µg β-GC with 15 µg β-LC |
| L | TNBS 0.5 mg × 2 | 15 µg β-LC |
| M | TNBS 0.5 mg × 2 | 150 µg β-LC |
| N | TNBS 0.5 mg × 2 | 1500 µg β-LC |
| O | — | 15 µg β-LC |
| P | — | 150 µg β-LC |
| Q | — | 1500 µg β-LC |

Example 5

β-Glycolipids for the Treatment of Non Alcoholic Steatohepatitis (NASH)

Effect of β-Glycolipids and Mixtures Thereof on Diabetes

To evaluate the effect of different β-glycolipids and mixtures thereof on diabetes, 12 groups of C57bl mice, consisting of 12 mice each are studied. Groups A-F mice are ob/ob mice, whereas Groups G-K are C57bl mice. Groups A-E and Groups G-K mice are injected intraperitoneally with 1.5 μg in 100 μl PBS every other day for 14 days with the following β-glycolipids: GluC (groups A,G), LacC (groups B, H), GalC (groups C, I), ceramide (groups D, J) and a mixture of GluC and LacC (groups F, L). Group F and Group L naïve ob/ob mice and naïve C57bl mice, respectively, are left untreated and serveas controls.

On the 14$^{th}$ day, glucose tolerance tests are performed on 6 mice from each group.

Effect of Orally Administered β-Glycolipids and Mixtures Thereof on NASH

To evaluate the effect of different β-glycolipids and mixtures thereof on the various metabolic and immunologic components of the NASH model, 12 groups of C57bl mice, consisting of 12 mice each are studied. Groups A-F mice are ob/ob mice, whereas Groups G-K are C57bl mice. Groups A-E and Groups G-K mice receive for 14 days oral daily amount of 15 μg of the following β-glycolipids: GluC (groups A,G), LacC (groups B, H), GalC (groups C, I), ceramide (groups D, J) and a mixture of GluC and LacC (groups F, L). Group F and Group L naïve ob/ob mice and naïve C57bl mice, respectively, are left untreated and serve as controls.

On the 14$^{th}$ day, glucose tolerance tests are performed on 6 mice from each group.

The Effect of β-Glycolipids on the Hepatic Fat Content

To determine the effect of β-glycolipids and mixtures thereof on hepatic fat content, 12 groups of C57bl mice, consisting of 12 mice each are studied. Groups A-F mice are ob/ob mice, whereas Groups G-K are C57bl mice. Groups A-E and Groups G-K mice are injected intraperitoneally with 1.5 μg in 100 μl PBS every other day for 14 days with the following β-glycolipids: GluC (groups A,G), LacC (groups B, H), GalC (groups C, I), ceramide (groups D, J) and a mixture of GluC and LacC (groups F, L). Group F and Group L naïve ob/ob mice and naïve C57bl mice, respectively, are left untreated and serve as controls.

To determine hepatic fat content, mice of all test groups undergoing an abdominal MRI on day 14 of the experiment. Hepatic fat content is determined and described as the SI index IP-OP/IP. Liver size, in area, is also determined.

Example 6

Mixed β-Glycolipids in Diabetic Pssamon Model

To determine the effect of a mixture of β-glucocerebroside and β-lactosyl-ceramide, on diabetes, the diabetic Passamon model is used. Three groups consisting of eight passamons each are used. Group A are injected with daily dose of 2.5 mg/kg β-glucocerebroside (five days a week), group B, are injected with daily dose of 2.5 mg/kg β-glucocerebroside+β-lactosyl-ceramide mixture, and group C injected with PBS and serves as a control group. On day 25, all passamons are sacrificed and examined by the following analysis:

Body and liver weight, glucose tolerance test, fasting serum levels of Insulin and Glucose for HOMA score, Western blot on splenocytes and liver lymphocytes for STAT proteins 1, 3, 4, 5, 6 and NFkB, biopsies from liver & pancreas for pathology, H&E stain, Oil Red O stain, biopsies from liver for RNA (in RNA later), serum for FFA, TG, Cholesterol, AST, ALT, GGT, insulin levels and MRI

Example 7

Mixed β-Glycolipids in Diabetes Using the Cohen Rat Model

To determine the effect of a mixture of β-glucocerebroside and β-lactosyl-ceramide, on diabetes, the Cohen rat model is used. Four groups consisting of ten rats each are used. All groups are fed with diabetic diet. Group A are injected with daily dose of 2.5 mg/kg β-glucocerebroside (five days a week), group B, are injected with daily dose of 2.5 mg/kg β-glucocerebroside+β-lactosyl-ceramide mixture, group C are injected with daily dose of 2.5 mg/kg β-lactosyl-ceramide and group D injected with PBS and serves as a control group.

Rats are analyzed as follows:
On day 1: rats are measured for weight
On day 15: Weight and post prandial glucose test (FFA at fasting 0.5 ml)
On day 30: Weight I.P/Oral GTT+insulin (FFA at fasting 0.5 ml), post prandial serum lipids and fasting serum levels of insulin and glucose for HOMA score.

All rats are sacrificed on day 30 and analyzed for total, liver and pancreas weight, MRI for determining the Fat (%) in the liver. Biopsies from liver and pancreas are taken for the following analysis:

H&E stain
Oil Red O stain
Biopsy in EM solution from pancreas
Biopsies from small bowel, kidney
Biopsies from liver for RNA (in RNA later)
Serum for FFA, TG, Cholesterol, AST, ALT, GGT
Serum for IFN, TGFβ, TNFα, IL2, IL4, IL10, IL12, Leptin, IL-1, IL-1β, IL-6, Adiponectin.
FACS for CD4+CD3+, CD8+CD3+, CD3+CD161+ from spleen and from the liver (not pooled)
Western for STAT 1, 4, 5, 6, NKkB, and SOCS proteins from spleen While various descriptions of the present invention are described above, it should be understood that the various features could be used singly or in any combination thereof. Therefore, this invention is not to be limited to only the specifically preferred embodiments depicted herein.

Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set-forth in the appended claims.

The invention claimed is:

1. A method of treating a mammal in need thereof, the method comprising administering two different lipids to the mammal, wherein the lipids are each selected from the group consisting of ceramide and a β-glycosylceramide, and wherein the mammal has colitis or a carcinoma.

2. The method of claim 1, wherein the mammal has hepatocellular carcinoma.

3. The method of claim 1, wherein the lipids are ceramide, β-glucosylceramide, β-galactosyl-ceramide, or β-lactosyl-ceramide, or a combination thereof.

4. The method of claim 1, wherein one of the two lipids is ceramide.

5. The method of claim 1, wherein one of the two lipids is β-glucosylceramide.

6. The method of claim 1, wherein one of the two lipids is β-galactosyl-ceramide.

7. The method of claim 1, wherein one of the two lipids is β-lactosyl-ceramide.

8. A pharmaceutical composition comprising two different compounds each selected from the group consisting of ceramide and a β-glycosylceramide, in a pharmaceutically acceptable excipient.

9. A method of treating a mammal in need thereof, the method comprising administering to the mammal a pharmaceutical composition of claim 8, wherein the mammal has colitis or a carcinoma.

10. The method of claim 9, wherein the mammal has hepatocellular carcinoma.

11. The method of claim 9, wherein the two different compounds are each selected from the group consisting of ceramide, β-glucosylceramide, β-galactosyl-ceramide, and β-lactosyl-ceramide.

12. The method of claim 9, wherein the two compounds are β-glucosylceramide and β-lactosyl-ceramide.

13. The method of claim 9, wherein the administering comprises oral, intravenous, intraperitoneal, intramuscular, parenteral, transdermal, intravaginal, intranasal, mucosal, sublingual, topical, rectal or subcutaneous administration, or any combination thereof.

14. The method of claim 1, wherein the administering comprises oral, intravenous, intraperitoneal, intramuscular, parenteral, transdermal, intravaginal, intranasal, mucosal, sublingual, topical, rectal or subcutaneous administration, or any combination thereof.

15. The pharmaceutical composition of claim 8, wherein the two different compounds are each selected from the group consisting of ceramide, β-glucosylceramide, β-galactosyl-ceramide, and β-lactosyl-ceramide.

16. The pharmaceutical composition of claim 8, wherein the two compounds are β-glucosylceramide and β-lactosyl-ceramide.

* * * * *

UNITED STATES PATENT AND TRADEMARK OFFICE
CERTIFICATE OF CORRECTION

Page 1 of 1

PATENT NO. : 7,897,580 B2
APPLICATION NO. : 11/287502
DATED : March 1, 2011
INVENTOR(S) : Yaron Ilan It is certified that error appears in the above-identified patent and that said Letters Patent is hereby corrected as shown below:

Correction of assignee information at Title page, at column 1, under "(75) Inventor: Yaron Ilan, Jerusalem (IL)," please insert the following:

-- (73) Assignee: Enzo Therapeutics, Inc., c/o Enzo Biochem, Inc. --

Signed and Sealed this
Seventh Day of July, 2015

Michelle K. Lee
*Director of the United States Patent and Trademark Office*